US009669149B2

(12) United States Patent
Anand

(10) Patent No.: US 9,669,149 B2
(45) Date of Patent: Jun. 6, 2017

(54) SPLITABLE TIP CATHETER WITH BIORESORBABLE ADHESIVE

(75) Inventor: Paramjith Anand, Lowell, MA (US)

(73) Assignee: Bard Access Systems, Inc., Salt Lake City, UT (US)

( * ) Notice: Subject to any disclaimer, the term of this patent is extended or adjusted under 35 U.S.C. 154(b) by 1006 days.

(21) Appl. No.: 12/048,871

(22) Filed: Mar. 14, 2008

(65) Prior Publication Data

US 2008/0214980 A1    Sep. 4, 2008

Related U.S. Application Data

(62) Division of application No. 10/874,298, filed on Jun. 9, 2004, now Pat. No. 8,992,454.

(51) Int. Cl.
| A61M 37/00 | (2006.01) |
| A61M 1/36 | (2006.01) |
| A61M 25/00 | (2006.01) |
| A61M 1/28 | (2006.01) |
| A61M 25/01 | (2006.01) |

(52) U.S. Cl.
CPC .......... *A61M 1/3661* (2014.02); *A61M 1/285* (2013.01); *A61M 25/003* (2013.01); *A61M 25/0026* (2013.01); *A61M 25/0068* (2013.01); *A61M 25/0071* (2013.01); *A61M 25/007* (2013.01); *A61M 25/008* (2013.01); *A61M 25/0032* (2013.01); *A61M 25/0074* (2013.01); *A61M 2025/0031* (2013.01); *A61M 2025/0034* (2013.01); *A61M 2025/0188* (2013.01)

(58) Field of Classification Search
CPC .......... A61M 25/0026; A61M 25/0071; A61M 1/285; A61M 2025/0034
USPC ...................... 604/4.01, 6.16, 5.01
See application file for complete search history.

(56) References Cited

U.S. PATENT DOCUMENTS

| 701,075 A | 5/1902 | McCully |
| 1,696,018 A | 12/1928 | Scheliberg |
| 1,856,811 A | 5/1932 | Inaki |
| 2,024,982 A | 12/1935 | Scott |
| 2,173,527 A | 9/1939 | Agayoff |
| 2,286,462 A | 6/1942 | Chaffin |
| 2,393,002 A | 1/1946 | Smith |
| 2,748,769 A | 6/1956 | Huber |

(Continued)

FOREIGN PATENT DOCUMENTS

| BE | 834211 | 2/1976 |
| CA | 1150122 | 7/1983 |

(Continued)

OTHER PUBLICATIONS

Arrow Cannon II Plus brochure (2006).

(Continued)

*Primary Examiner* — Susan Su
(74) *Attorney, Agent, or Firm* — Rutan & Tucker, LLP

(57) ABSTRACT

Splitable-tip catheters are disclosed with bioresorbable adhesive to provide spatial separation of distal tip elements during use. The invention can be particularly useful in hemodialysis applications where it is desirable to separate blood extraction and return lumens. The adhesive facilitates insertion of the distal end of the catheter as an assembly, e.g., into a blood vessel using a single guidewire, while the bioresorbable nature of the adhesive allows the tip elements to separate in vivo.

25 Claims, 12 Drawing Sheets

(56) References Cited

U.S. PATENT DOCUMENTS

| | | |
|---|---|---|
| 2,910,981 A | 11/1959 | Wilson et al. |
| 3,144,868 A | 8/1964 | Jascalevich |
| 3,176,690 A | 4/1965 | H'Doubler |
| 3,256,885 A | 6/1966 | Higgins et al. |
| 3,308,822 A | 3/1967 | De Luca |
| 3,416,532 A | 12/1968 | Grossman |
| 3,426,759 A | 2/1969 | Smith |
| 3,460,255 A | 8/1969 | Hutson |
| D217,795 S | 6/1970 | Spaven |
| 3,612,038 A | 10/1971 | Halligan |
| 3,736,939 A | 6/1973 | Taylor |
| 3,805,794 A | 4/1974 | Schlesinger |
| 3,812,851 A | 5/1974 | Rodriguez |
| 3,848,604 A | 11/1974 | Sackner |
| 3,890,977 A | 6/1975 | Wilson |
| 3,929,126 A | 12/1975 | Corsaut |
| 3,935,857 A | 2/1976 | Co |
| 3,995,623 A | 12/1976 | Blake et al. |
| 4,068,659 A | 1/1978 | Moorehead |
| 4,072,146 A | 2/1978 | Howes |
| 4,072,153 A | 2/1978 | Swartz |
| 4,098,275 A | 7/1978 | Consalvo |
| 4,114,625 A | 9/1978 | Onat |
| 4,117,836 A | 10/1978 | Erikson et al. |
| 4,129,129 A | 12/1978 | Amrine |
| 4,134,402 A | 1/1979 | Mahurkar |
| 4,149,535 A | 4/1979 | Volder et al. |
| 4,180,068 A | 12/1979 | Jacobsen et al. |
| D254,444 S | 3/1980 | Levine |
| 4,248,224 A | 2/1981 | Jones |
| 4,276,880 A | 7/1981 | Malmin |
| 4,292,976 A | 10/1981 | Banka |
| 4,299,228 A | 11/1981 | Peters |
| 4,300,550 A | 11/1981 | Gandi et al. |
| 4,309,994 A | 1/1982 | Grunwald |
| 4,327,722 A | 5/1982 | Groshong et al. |
| 4,385,631 A | 5/1983 | Uthmann |
| 4,392,855 A | 7/1983 | Oreopoulos et al. |
| 4,403,983 A | 9/1983 | Edelman et al. |
| 4,405,313 A | 9/1983 | Sisley et al. |
| 4,406,656 A | 9/1983 | Hattler et al. |
| D272,651 S | 2/1984 | Mahurkar |
| 4,431,426 A | 2/1984 | Groshong et al. |
| 4,432,722 A | 2/1984 | Bohan, Jr. et al. |
| 4,432,752 A | 2/1984 | Marlon |
| 4,445,893 A | 5/1984 | Bodicky |
| 4,451,252 A | 5/1984 | Martin |
| 4,453,928 A | 6/1984 | Steiger |
| 4,465,482 A | 8/1984 | Tittel et al. |
| 4,490,138 A | 12/1984 | Lipsky et al. |
| 4,493,696 A | 1/1985 | Uldall |
| RE31,873 E | 4/1985 | Howes |
| 4,531,933 A | 7/1985 | Norton et al. |
| 4,543,087 A | 9/1985 | Sommercorn et al. |
| 4,545,373 A | 10/1985 | Christoudias |
| 4,549,879 A | 10/1985 | Groshong et al. |
| 4,557,261 A | 12/1985 | Rugheimer et al. |
| 4,568,329 A | 2/1986 | Mahurkar |
| 4,568,338 A | 2/1986 | Todd |
| 4,573,476 A | 3/1986 | Ruiz |
| 4,581,012 A | 4/1986 | Brown et al. |
| 4,583,968 A | 4/1986 | Mahurkar |
| 4,583,986 A | 4/1986 | Lapidus |
| 4,601,697 A | 7/1986 | Mammolenti et al. |
| 4,619,643 A | 10/1986 | Bai |
| 4,623,327 A | 11/1986 | Mahurkar |
| 4,626,240 A | 12/1986 | Edelman et al. |
| 4,642,101 A | 2/1987 | Krolikowski et al. |
| 4,643,711 A | 2/1987 | Bates |
| 4,666,426 A | 5/1987 | Aigner et al. |
| 4,668,221 A | 5/1987 | Luther |
| 4,670,009 A | 6/1987 | Bullock |
| 4,675,004 A | 6/1987 | Hadford et al. |
| 4,681,122 A | 7/1987 | Winters et al. |
| 4,681,564 A | 7/1987 | Landreneau |
| 4,681,570 A | 7/1987 | Dalton |
| 4,682,978 A | 7/1987 | Martin |
| 4,687,471 A | 8/1987 | Twardowski et al. |
| 4,692,141 A | 9/1987 | Mahurkar |
| 4,694,838 A | 9/1987 | Wijayarthna et al. |
| 4,701,159 A | 10/1987 | Brown et al. |
| 4,702,917 A | 10/1987 | Schindler |
| 4,706,671 A | 11/1987 | Weinrib |
| 4,713,171 A | 12/1987 | Polaschegg |
| 4,717,379 A | 1/1988 | Ekholmer et al. |
| 4,735,620 A | 4/1988 | Ruiz |
| 4,737,141 A | 4/1988 | Spits |
| 4,737,152 A | 4/1988 | Alchas |
| 4,738,667 A | 4/1988 | Galloway |
| 4,748,808 A | 6/1988 | Hill |
| 4,755,176 A | 7/1988 | Patel |
| 4,769,016 A | 9/1988 | Labianca |
| 4,770,652 A | 9/1988 | Mahurkar |
| 4,772,268 A | 9/1988 | Bates |
| 4,772,269 A | 9/1988 | Twardowski et al. |
| 4,776,841 A | 10/1988 | Catalano |
| 4,777,951 A | 10/1988 | Cribier et al. |
| 4,784,638 A | 11/1988 | Ghajar et al. |
| 4,790,809 A | 12/1988 | Kuntz |
| 4,795,439 A | 1/1989 | Guest |
| 4,801,297 A | 1/1989 | Mueller |
| D300,060 S | 2/1989 | Molgaard-Nielsen |
| 4,804,359 A | 2/1989 | Grunwald et al. |
| 4,808,155 A | 2/1989 | Mahurkar |
| 4,808,163 A | 2/1989 | Laub |
| 4,809,710 A | 3/1989 | Williamson |
| 4,820,265 A | 4/1989 | DeSatnick et al. |
| 4,832,687 A | 5/1989 | Smith, III |
| 4,834,709 A | 5/1989 | Banning et al. |
| 4,842,582 A | 6/1989 | Mahurkar |
| 4,842,592 A | 6/1989 | Caggiani et al. |
| 4,846,814 A | 7/1989 | Ruiz |
| 4,863,441 A | 9/1989 | Lindsay et al. |
| 4,867,742 A | 9/1989 | Calderon |
| 4,892,518 A | 1/1990 | Cupp et al. |
| 4,894,057 A | 1/1990 | Howes |
| 4,895,561 A | 1/1990 | Mahurkar |
| 4,898,591 A | 2/1990 | Jang et al. |
| 4,906,238 A | 3/1990 | Greenfeld et al. |
| 4,925,452 A | 5/1990 | Melinyshyn et al. |
| 4,927,418 A | 5/1990 | Dake et al. |
| 4,935,004 A | 6/1990 | Cruz |
| 4,935,010 A | 6/1990 | Cox et al. |
| 4,935,044 A | 6/1990 | Schoenpflug et al. |
| 4,936,826 A | 6/1990 | Amarasinghe |
| 4,950,232 A | 8/1990 | Ruzicka et al. |
| 4,950,259 A | 8/1990 | Geary et al. |
| 4,951,665 A | 8/1990 | Schneider |
| 4,961,729 A | 10/1990 | Vaillancourt |
| 4,961,731 A | 10/1990 | Bodicky et al. |
| 4,961,809 A | 10/1990 | Martin |
| 4,968,307 A | 11/1990 | Dake et al. |
| 4,969,890 A | 11/1990 | Sugita et al. |
| 4,981,477 A | 1/1991 | Schon et al. |
| 4,985,014 A | 1/1991 | Orejola |
| 4,990,138 A | 2/1991 | Bacich et al. |
| 4,994,027 A | 2/1991 | Farrell |
| 4,995,865 A | 2/1991 | Gahara et al. |
| 5,009,636 A | 4/1991 | Wortley et al. |
| 5,015,230 A | 5/1991 | Martin et al. |
| 5,016,640 A | 5/1991 | Ruiz |
| 5,021,044 A | 6/1991 | Sharkawy |
| 5,041,101 A | 8/1991 | Seder et al. |
| 5,041,107 A | 8/1991 | Heil, Jr. |
| 5,049,138 A * | 9/1991 | Chevalier et al. ............ 604/265 |
| 5,053,003 A | 10/1991 | Dadson et al. |
| 5,053,004 A | 10/1991 | Markel et al. |
| 5,053,023 A | 10/1991 | Martin |
| 5,057,073 A | 10/1991 | Martin |
| 5,059,170 A | 10/1991 | Cameron |
| 5,059,177 A | 10/1991 | Towne et al. |
| 5,069,673 A | 12/1991 | Shwab |
| 5,074,841 A | 12/1991 | Ademovic et al. |
| 5,084,013 A | 1/1992 | Takase et al. |

(56) References Cited

U.S. PATENT DOCUMENTS

| | | |
|---|---|---|
| 5,098,412 A | 3/1992 | Shiu |
| 5,100,395 A | 3/1992 | Rosenberg |
| 5,102,402 A | 4/1992 | Dror et al. |
| 5,106,368 A | 4/1992 | Uldall et al. |
| 5,106,376 A | 4/1992 | Mononen et al. |
| 5,111,829 A * | 5/1992 | Alvarez de Toledo ....... 600/585 |
| 5,112,301 A | 5/1992 | Fenton, Jr. et al. |
| 5,114,423 A | 5/1992 | Kasprzyk et al. |
| 5,117,836 A | 6/1992 | Millar |
| 5,120,299 A | 6/1992 | Lombardi |
| 5,120,304 A | 6/1992 | Sasaki |
| 5,122,125 A | 6/1992 | Deuss et al. |
| 5,125,888 A * | 6/1992 | Howard ............ A61M 25/0105 600/12 |
| 5,125,904 A | 6/1992 | Lee |
| 5,129,891 A | 7/1992 | Young |
| 5,135,599 A | 8/1992 | Martin et al. |
| 5,139,486 A | 8/1992 | Moss |
| 5,156,592 A | 10/1992 | Martin et al. |
| 5,163,928 A | 11/1992 | Hobbs et al. |
| 5,167,623 A | 12/1992 | Cianci et al. |
| 5,171,216 A | 12/1992 | Dasse et al. |
| 5,171,227 A | 12/1992 | Twardowski et al. |
| 5,178,616 A | 1/1993 | Uemiya et al. |
| 5,188,592 A | 2/1993 | Hakki |
| 5,188,593 A | 2/1993 | Martin |
| 5,190,520 A | 3/1993 | Fenton, Jr. et al. |
| 5,190,529 A | 3/1993 | McCrory et al. |
| 5,191,898 A | 3/1993 | Millar |
| 5,195,962 A | 3/1993 | Martin et al. |
| 5,197,951 A | 3/1993 | Mahurkar |
| 5,197,973 A | 3/1993 | Pang et al. |
| 5,197,976 A | 3/1993 | Herweck et al. |
| 5,207,648 A | 5/1993 | Gross |
| 5,207,650 A | 5/1993 | Martin |
| 5,209,723 A | 5/1993 | Twardowski et al. |
| 5,209,725 A | 5/1993 | Roth |
| 5,209,742 A | 5/1993 | Venema et al. |
| 5,215,527 A | 6/1993 | Beck et al. |
| 5,221,255 A | 6/1993 | Mahurkar et al. |
| 5,221,256 A | 6/1993 | Mahurkar |
| 5,222,949 A | 6/1993 | Kaldany |
| 5,226,880 A | 7/1993 | Martin et al. |
| 5,234,438 A | 8/1993 | Semrad |
| 5,236,016 A | 8/1993 | Vogelsang et al. |
| 5,242,398 A | 9/1993 | Knoll et al. |
| 5,246,430 A | 9/1993 | MacFarlane |
| 5,250,034 A | 10/1993 | Appling et al. |
| 5,254,084 A | 10/1993 | Geary |
| 5,273,527 A | 12/1993 | Schatz et al. |
| 5,273,534 A | 12/1993 | Knoepfler |
| 5,279,596 A | 1/1994 | Castaneda et al. |
| 5,279,599 A | 1/1994 | Wilk |
| 5,306,240 A | 4/1994 | Berry |
| 5,312,337 A | 5/1994 | Flaherty et al. |
| 5,312,357 A | 5/1994 | Buijs et al. |
| 5,318,517 A | 6/1994 | Reiman |
| 5,322,519 A | 6/1994 | Ash |
| 5,324,274 A | 6/1994 | Martin |
| 5,330,432 A | 7/1994 | Yoon |
| 5,338,308 A | 8/1994 | Wilk |
| 5,342,295 A | 8/1994 | Imran |
| 5,342,386 A | 8/1994 | Trotta |
| 5,346,471 A | 9/1994 | Raulerson |
| 5,348,536 A | 9/1994 | Young et al. |
| 5,350,358 A | 9/1994 | Martin |
| 5,360,397 A | 11/1994 | Pinchuk |
| 5,360,407 A | 11/1994 | Leonard et al. |
| 5,364,344 A | 11/1994 | Beattie et al. |
| 5,374,245 A | 12/1994 | Mahurkar |
| 5,378,230 A | 1/1995 | Mahurkar |
| 5,380,276 A | 1/1995 | Miller et al. |
| 5,380,290 A | 1/1995 | Makower et al. |
| 5,382,238 A | 1/1995 | Abrahamson et al. |
| 5,389,087 A | 2/1995 | Miraki |
| 5,389,090 A | 2/1995 | Fischell et al. |
| 5,395,316 A | 3/1995 | Martin et al. |
| 5,399,168 A | 3/1995 | Wadsworth, Jr. et al. |
| 5,403,291 A | 4/1995 | Abrahamson |
| 5,405,320 A | 4/1995 | Twardowski et al. |
| 5,405,341 A | 4/1995 | Martin |
| 5,409,463 A | 4/1995 | Thomas et al. |
| 5,417,668 A | 5/1995 | Setzer et al. |
| 5,423,768 A | 6/1995 | Folden et al. |
| 5,431,661 A | 7/1995 | Koch |
| 5,451,026 A | 9/1995 | Smith |
| 5,451,206 A | 9/1995 | Young |
| 5,451,233 A | 9/1995 | Yock |
| 5,458,570 A * | 10/1995 | May, Jr. ........................ 604/500 |
| 5,458,582 A | 10/1995 | Nakao |
| 5,462,533 A | 10/1995 | Daugherty |
| 5,472,417 A | 12/1995 | Martin et al. |
| 5,472,432 A | 12/1995 | Martin |
| 5,476,453 A | 12/1995 | Mehta |
| 5,480,380 A | 1/1996 | Martin |
| 5,486,159 A | 1/1996 | Mahurkar |
| 5,489,278 A | 2/1996 | Abrahamson |
| 5,496,292 A | 3/1996 | Burnham |
| 5,496,872 A | 3/1996 | Constancis et al. |
| 5,505,710 A | 4/1996 | Dorsey, III |
| 5,507,723 A | 4/1996 | Keshaviah |
| 5,509,897 A | 4/1996 | Twardowski et al. |
| 5,509,900 A | 4/1996 | Kirkman |
| 5,509,902 A | 4/1996 | Raulerson |
| 5,542,925 A | 8/1996 | Orth |
| 5,545,373 A | 8/1996 | Maziasz et al. |
| 5,556,390 A | 9/1996 | Hicks |
| 5,556,930 A | 9/1996 | Brehm et al. |
| 5,558,635 A | 9/1996 | Cannon |
| 5,562,609 A | 10/1996 | Brumbach |
| 5,562,696 A | 10/1996 | Nobles et al. |
| 5,569,182 A | 10/1996 | Twardowski et al. |
| 5,569,195 A | 10/1996 | Saab |
| 5,571,093 A | 11/1996 | Cruz et al. |
| 5,584,803 A | 12/1996 | Stevens et al. |
| 5,599,304 A | 2/1997 | Shaari |
| 5,599,328 A | 2/1997 | Stevens |
| 5,607,462 A | 3/1997 | Imran |
| 5,624,392 A | 4/1997 | Saab |
| 5,624,413 A | 4/1997 | Markel et al. |
| 5,632,729 A | 5/1997 | Cai et al. |
| 5,637,102 A | 6/1997 | Tolkoff et al. |
| 5,642,270 A | 6/1997 | Green et al. |
| 5,662,606 A | 9/1997 | Cimino et al. |
| 5,665,067 A | 9/1997 | Linder et al. |
| 5,674,237 A | 10/1997 | Ott |
| 5,685,867 A | 11/1997 | Twardowski et al. |
| 5,686,867 A | 11/1997 | Sutardja et al. |
| 5,693,030 A | 12/1997 | Lee et al. |
| 5,695,457 A | 12/1997 | St. Goar et al. |
| 5,704,915 A | 1/1998 | Melsky et al. |
| 5,713,849 A | 2/1998 | Bosma et al. |
| 5,713,853 A | 2/1998 | Clark et al. |
| 5,717,216 A | 2/1998 | McCoy et al. |
| 5,718,678 A | 2/1998 | Fleming, III |
| 5,718,692 A | 2/1998 | Schon et al. |
| 5,720,735 A | 2/1998 | Dorros |
| 5,738,649 A | 4/1998 | Macoviak |
| 5,741,329 A * | 4/1998 | Agrawal et al. .............. 424/423 |
| 5,743,873 A | 4/1998 | Cai et al. |
| 5,752,939 A | 5/1998 | Makoto et al. |
| 5,769,796 A | 6/1998 | Palermo et al. |
| 5,772,643 A | 6/1998 | Howell et al. |
| 5,776,096 A | 7/1998 | Fields |
| 5,776,111 A | 7/1998 | Tesio |
| 5,785,686 A | 7/1998 | Runge |
| 5,792,094 A | 8/1998 | Stevens et al. |
| 5,792,123 A | 8/1998 | Ensminger |
| 5,797,869 A | 8/1998 | Martin et al. |
| 5,800,384 A | 9/1998 | Russell et al. |
| 5,800,414 A | 9/1998 | Cazal |
| 5,800,516 A * | 9/1998 | Fine et al. ..................... 128/898 |
| 5,807,311 A | 9/1998 | Palestrant |
| 5,807,318 A | 9/1998 | St. Goar et al. |

(56) References Cited

U.S. PATENT DOCUMENTS

| | | |
|---|---|---|
| 5,807,329 A | 9/1998 | Gelman |
| 5,809,897 A | 9/1998 | Powell et al. |
| 5,810,789 A | 9/1998 | Powers et al. |
| 5,814,016 A | 9/1998 | Valley et al. |
| 5,830,184 A | 11/1998 | Basta |
| 5,830,196 A | 11/1998 | Hicks |
| 5,833,671 A | 11/1998 | Macoviak et al. |
| 5,843,048 A | 12/1998 | Gross |
| 5,858,009 A | 1/1999 | Jonkman |
| 5,861,010 A | 1/1999 | Boussignac et al. |
| 5,868,717 A | 2/1999 | Prosl |
| 5,873,865 A | 2/1999 | Horzewski et al. |
| 5,876,366 A | 3/1999 | Dykstra et al. |
| 5,876,426 A | 3/1999 | Kume et al. |
| 5,882,347 A | 3/1999 | Mouris-Laan et al. |
| 5,891,111 A | 4/1999 | Ismael et al. |
| 5,904,670 A | 5/1999 | Schreiner |
| 5,911,715 A | 6/1999 | Berg et al. |
| 5,913,848 A | 6/1999 | Luther et al. |
| 5,916,208 A | 6/1999 | Luther et al. |
| 5,919,160 A | 7/1999 | Sanfilippo, II |
| 5,944,732 A | 8/1999 | Raulerson et al. |
| 5,947,937 A | 9/1999 | Urrutia et al. |
| 5,947,953 A | 9/1999 | Ash et al. |
| 5,957,879 A | 9/1999 | Roberts et al. |
| 5,957,893 A | 9/1999 | Luther et al. |
| 5,957,912 A | 9/1999 | Heitzmann |
| 5,961,486 A | 10/1999 | Twardowski et al. |
| 5,964,796 A | 10/1999 | Imran |
| 5,976,103 A | 11/1999 | Martin |
| 5,976,120 A | 11/1999 | Chow et al. |
| 5,980,551 A | 11/1999 | Summers et al. |
| 5,984,908 A | 11/1999 | Davis et al. |
| 5,989,206 A | 11/1999 | Prosl et al. |
| 5,989,213 A | 11/1999 | Maginot |
| 6,001,079 A | 12/1999 | Pourchez |
| 6,033,382 A | 3/2000 | Basta |
| 6,036,654 A | 3/2000 | Quinn et al. |
| 6,059,771 A | 5/2000 | Balbierz et al. |
| 6,074,374 A | 6/2000 | Fulton |
| 6,086,555 A | 7/2000 | Eliasen et al. |
| 6,086,557 A | 7/2000 | Morejohn et al. |
| 6,090,096 A | 7/2000 | St. Goar et al. |
| 6,099,513 A | 8/2000 | Spehalski |
| 6,103,778 A * | 8/2000 | Hyon et al. .................. 523/111 |
| 6,106,540 A | 8/2000 | White et al. |
| 6,113,572 A | 9/2000 | Gailey et al. |
| 6,117,117 A | 9/2000 | Mauch |
| 6,120,494 A | 9/2000 | Jonkman |
| 6,126,631 A | 10/2000 | Loggie |
| 6,132,425 A | 10/2000 | Gough |
| 6,143,013 A | 11/2000 | Samson et al. |
| 6,146,354 A | 11/2000 | Beil |
| 6,146,373 A | 11/2000 | Cragg et al. |
| 6,152,909 A | 11/2000 | Bagaoisan et al. |
| 6,156,016 A | 12/2000 | Maginot |
| 6,161,547 A | 12/2000 | Barbut |
| 6,178,356 B1 | 1/2001 | Chastain et al. |
| 6,180,059 B1 | 1/2001 | Divino, Jr. et al. |
| 6,190,349 B1 | 2/2001 | Ash et al. |
| 6,190,371 B1 | 2/2001 | Maginot et al. |
| 6,193,685 B1 | 2/2001 | Goodin |
| 6,196,996 B1 | 3/2001 | Teirstein |
| 6,206,849 B1 | 3/2001 | Martin et al. |
| 6,210,365 B1 | 4/2001 | Afzal |
| 6,210,380 B1 | 4/2001 | Mauch |
| 6,217,527 B1 | 4/2001 | Selmon et al. |
| 6,224,622 B1 * | 5/2001 | Kotzev .................. 606/214 |
| 6,238,406 B1 | 5/2001 | Ellis et al. |
| 6,264,627 B1 | 7/2001 | Liska et al. |
| 6,273,879 B1 | 8/2001 | Keith et al. |
| 6,280,413 B1 | 8/2001 | Clark et al. |
| 6,280,423 B1 | 8/2001 | Davey et al. |
| 6,287,326 B1 | 9/2001 | Pecor |
| 6,293,927 B1 | 9/2001 | McGuckin, Jr. |
| 6,293,958 B1 | 9/2001 | Berry et al. |
| 6,296,631 B2 | 10/2001 | Chow |
| 6,299,631 B1 | 10/2001 | Shalaby |
| 6,322,551 B1 | 11/2001 | Brugger |
| 6,328,730 B1 | 12/2001 | Harkrider, Jr. |
| 6,342,120 B1 | 1/2002 | Basta |
| 6,361,529 B1 | 3/2002 | Goodin et al. |
| 6,383,172 B1 | 5/2002 | Barbut |
| 6,394,141 B2 | 5/2002 | Wages et al. |
| 6,394,142 B1 | 5/2002 | Woelfel et al. |
| 6,409,700 B1 | 6/2002 | Siegel, Jr. et al. |
| 6,413,228 B1 | 7/2002 | Hung et al. |
| 6,428,513 B1 | 8/2002 | Abrahamson |
| 6,443,922 B1 | 9/2002 | Roberts et al. |
| 6,450,988 B1 | 9/2002 | Bradshaw |
| 6,453,185 B1 | 9/2002 | O'Keefe |
| 6,454,997 B1 | 9/2002 | Divino, Jr. et al. |
| 6,455,608 B1 | 9/2002 | Jia et al. |
| 6,463,335 B1 | 10/2002 | Munch et al. |
| 6,468,287 B1 | 10/2002 | Baugh |
| 6,473,633 B1 | 10/2002 | Heil, Jr. et al. |
| 6,475,207 B1 | 11/2002 | Maginot et al. |
| 6,475,209 B1 | 11/2002 | Larson et al. |
| 6,478,789 B1 | 11/2002 | Spehalski et al. |
| 6,482,169 B1 | 11/2002 | Kuhle |
| 6,533,763 B1 | 3/2003 | Schneiter |
| 6,565,594 B1 | 5/2003 | Herweck et al. |
| 6,576,001 B2 | 6/2003 | Werneth et al. |
| 6,582,459 B1 | 6/2003 | Lau et al. |
| 6,585,705 B1 | 7/2003 | Maginot et al. |
| 6,592,565 B2 | 7/2003 | Twardowski |
| 6,595,966 B2 | 7/2003 | Davey et al. |
| 6,620,118 B1 | 9/2003 | Prosl et al. |
| 6,638,242 B2 | 10/2003 | Wilson et al. |
| 6,659,134 B2 | 12/2003 | Navis |
| 6,682,498 B2 | 1/2004 | Ross |
| 6,682,519 B1 | 1/2004 | Schon |
| 6,691,625 B2 | 2/2004 | Duncan |
| 6,695,832 B2 | 2/2004 | Schon et al. |
| 6,702,776 B2 | 3/2004 | Quinn |
| 6,712,797 B1 | 3/2004 | Southern, Jr. |
| 6,712,798 B2 | 3/2004 | Constantz |
| 6,719,717 B1 | 4/2004 | Johnson et al. |
| 6,719,749 B1 | 4/2004 | Schweikert et al. |
| 6,723,084 B1 | 4/2004 | Maginot et al. |
| 6,723,114 B2 * | 4/2004 | Shalaby .................. 606/214 |
| 6,730,299 B1 * | 5/2004 | Tayot et al. .................. 424/45 |
| 6,752,827 B2 | 6/2004 | Ross et al. |
| 6,755,851 B2 | 6/2004 | Noda et al. |
| 6,758,836 B2 | 7/2004 | Zawacki |
| 6,786,664 B2 | 9/2004 | Claramunt et al. |
| 6,786,884 B1 | 9/2004 | DeCant, Jr. et al. |
| 6,796,991 B2 | 9/2004 | Nardeo |
| 6,797,107 B1 * | 9/2004 | Kotzev .................. 156/331.1 |
| 6,808,510 B1 | 10/2004 | DiFiore |
| 6,814,718 B2 | 11/2004 | McGuckin, Jr. et al. |
| 6,819,951 B2 | 11/2004 | Patel et al. |
| 6,821,287 B1 | 11/2004 | Jang |
| 6,824,554 B1 | 11/2004 | Jang |
| 6,835,452 B1 | 12/2004 | Hamerski |
| 6,837,864 B1 | 1/2005 | Bertolero et al. |
| 6,852,079 B2 | 2/2005 | Miyano |
| 6,852,097 B1 | 2/2005 | Fulton, III |
| 6,858,019 B2 | 2/2005 | McGuckin, Jr. et al. |
| 6,872,198 B1 | 3/2005 | Wilson et al. |
| 6,878,143 B2 | 4/2005 | Andersen |
| 6,881,211 B2 | 4/2005 | Schweikert et al. |
| 6,884,253 B1 | 4/2005 | McFarlane |
| 6,911,014 B2 | 6/2005 | Wentling et al. |
| 6,913,601 B2 | 7/2005 | St. Goar et al. |
| 6,916,313 B2 | 7/2005 | Cunningham |
| 6,921,396 B1 | 7/2005 | Wilson et al. |
| 6,921,411 B2 | 7/2005 | Yock |
| 6,934,142 B2 | 8/2005 | Grosse et al. |
| 6,966,886 B2 | 11/2005 | Appling |
| 6,969,381 B2 | 11/2005 | Voorhees |
| 6,979,318 B1 | 12/2005 | McDonald et al. |
| 6,991,625 B1 | 1/2006 | Gately et al. |
| D515,211 S | 2/2006 | Chesnin |

(56) References Cited

U.S. PATENT DOCUMENTS

| | | |
|---|---|---|
| 6,997,894 B2 | 2/2006 | Caresio |
| 7,008,395 B1 | 3/2006 | Loggie |
| 7,011,645 B2 | 3/2006 | McGuckin, Jr. et al. |
| 7,018,384 B2 | 3/2006 | Skakoon |
| 7,029,467 B2 | 4/2006 | Currier et al. |
| 7,066,914 B2 | 6/2006 | Andersen |
| 7,066,925 B2 | 6/2006 | Gately et al. |
| 7,074,213 B2 | 7/2006 | McGuckin, Jr. et al. |
| 7,077,829 B2 | 7/2006 | McGuckin, Jr. et al. |
| 7,087,053 B2 | 8/2006 | Vanney |
| 7,090,654 B2 | 8/2006 | Lotito et al. |
| 7,108,674 B2 | 9/2006 | Quinn |
| D530,420 S | 10/2006 | Chesnin |
| 7,128,734 B1 | 10/2006 | Wilson et al. |
| 7,130,700 B2 | 10/2006 | Gardeski et al. |
| 7,141,035 B2 | 11/2006 | Haggstrom |
| RE39,451 E | 12/2006 | Kuhle |
| 7,182,746 B2 | 2/2007 | Haarala et al. |
| 7,300,430 B2 | 11/2007 | Wilson et al. |
| 7,322,953 B2 | 1/2008 | Redinger |
| 7,347,852 B2 | 3/2008 | Hobbs et al. |
| 7,381,204 B2 | 6/2008 | Wilson et al. |
| 7,393,339 B2 | 7/2008 | Zawacki et al. |
| 7,422,571 B2 | 9/2008 | Schweikert et al. |
| 7,465,286 B2 | 12/2008 | Patterson et al. |
| 7,485,107 B2 | 2/2009 | DiFiore et al. |
| 7,569,029 B2 | 8/2009 | Clark |
| 7,575,563 B2 | 8/2009 | Appling |
| 7,651,482 B2 | 1/2010 | Harris |
| 7,686,823 B2 | 3/2010 | Pingleton et al. |
| 7,798,999 B2 | 9/2010 | Bailey et al. |
| 7,972,465 B2 | 7/2011 | Patterson et al. |
| 8,021,321 B2 | 9/2011 | Zawacki |
| 8,066,660 B2 | 11/2011 | Gregersen et al. |
| 8,092,415 B2 | 1/2012 | Moehle |
| 8,100,863 B2 | 1/2012 | Moehle et al. |
| 8,152,951 B2 | 4/2012 | Zawacki et al. |
| 8,206,371 B2 | 6/2012 | Nimkar et al. |
| 8,292,841 B2 | 10/2012 | Gregersen |
| 8,500,939 B2 | 8/2013 | Nimkar et al. |
| 8,540,661 B2 | 9/2013 | Gregersen |
| 8,597,275 B2 | 12/2013 | Nimkar et al. |
| 8,696,614 B2 | 4/2014 | Gregersen et al. |
| 8,808,227 B2 | 8/2014 | Zawacki et al. |
| 8,894,601 B2 | 11/2014 | Moehle et al. |
| 8,992,454 B2 | 3/2015 | Anand |
| 9,572,956 B2 | 2/2017 | Nimkar et al. |
| 9,579,485 B2 | 2/2017 | Oborn et al. |
| 9,610,422 B2 | 4/2017 | Moehle et al. |
| 2001/0041857 A1 | 11/2001 | Sansoucy |
| 2001/0041873 A1 | 11/2001 | Dopper et al. |
| 2002/0013569 A1 | 1/2002 | Sterman et al. |
| 2002/0026156 A1 | 2/2002 | Quinn |
| 2002/0055724 A1* | 5/2002 | Hughes .................. A61B 19/00 604/294 |
| 2002/0086047 A1 | 7/2002 | Mueller et al. |
| 2002/0087145 A1 | 7/2002 | Ehwald et al. |
| 2002/0091362 A1 | 7/2002 | Maginot et al. |
| 2002/0091430 A1 | 7/2002 | Dobak et al. |
| 2002/0099326 A1 | 7/2002 | Wilson et al. |
| 2002/0099327 A1 | 7/2002 | Wilson et al. |
| 2002/0107506 A1 | 8/2002 | McGuckin et al. |
| 2002/0138031 A1 | 9/2002 | Ross |
| 2002/0169490 A1 | 11/2002 | Noda et al. |
| 2002/0173770 A1* | 11/2002 | Flory ............... A61B 17/00491 604/537 |
| 2002/0177904 A1 | 11/2002 | Huxel et al. |
| 2003/0023198 A1 | 1/2003 | Twardowski |
| 2003/0032734 A1 | 2/2003 | Roby |
| 2003/0088213 A1 | 5/2003 | Schweikert et al. |
| 2003/0093027 A1 | 5/2003 | McGuckin et al. |
| 2003/0097091 A1 | 5/2003 | Hobbs et al. |
| 2003/0135147 A1 | 7/2003 | Rosenberg et al. |
| 2003/0144623 A1 | 7/2003 | Heath et al. |
| 2003/0149395 A1 | 8/2003 | Zawacki |
| 2003/0153898 A1 | 8/2003 | Schon et al. |
| 2003/0163145 A1 | 8/2003 | Raulerson |
| 2003/0187411 A1 | 10/2003 | Constantz |
| 2003/0204179 A1 | 10/2003 | Davey et al. |
| 2004/0039350 A1 | 2/2004 | McKittrick |
| 2004/0054321 A1 | 3/2004 | Schon et al. |
| 2004/0059314 A1 | 3/2004 | Schon et al. |
| 2004/0064086 A1 | 4/2004 | Gottlieb et al. |
| 2004/0065333 A1 | 4/2004 | Wilson et al. |
| 2004/0075198 A1 | 4/2004 | Schweikert et al. |
| 2004/0087892 A1* | 5/2004 | Cunningham .................. 604/43 |
| 2004/0092863 A1 | 5/2004 | Raulerson et al. |
| 2004/0097863 A1 | 5/2004 | Appling |
| 2004/0097903 A1 | 5/2004 | Raulerson |
| 2004/0122418 A1 | 6/2004 | Voorhees |
| 2004/0147903 A1 | 7/2004 | Latini |
| 2004/0167463 A1* | 8/2004 | Zawacki et al. .................. 604/43 |
| 2004/0171997 A1 | 9/2004 | Wilson et al. |
| 2004/0172003 A1 | 9/2004 | Wilson et al. |
| 2004/0176739 A1 | 9/2004 | Stephens et al. |
| 2004/0193102 A1 | 9/2004 | Haggstrom |
| 2004/0197301 A1 | 10/2004 | Zhao et al. |
| 2004/0210180 A1 | 10/2004 | Altman |
| 2004/0210187 A1 | 10/2004 | Zawacki |
| 2004/0210237 A1 | 10/2004 | Ross et al. |
| 2004/0220550 A1 | 11/2004 | Schryver |
| 2004/0230204 A1 | 11/2004 | Wortley et al. |
| 2004/0243095 A1 | 12/2004 | Nimkar et al. |
| 2004/0249337 A1 | 12/2004 | DiFiore |
| 2005/0003322 A1 | 1/2005 | Logan et al. |
| 2005/0004504 A1 | 1/2005 | Frye et al. |
| 2005/0013341 A1 | 1/2005 | Baghai |
| 2005/0019382 A1 | 1/2005 | Kummer et al. |
| 2005/0025641 A1 | 2/2005 | Shibata et al. |
| 2005/0027282 A1 | 2/2005 | Schweikert et al. |
| 2005/0027289 A1 | 2/2005 | Castellano et al. |
| 2005/0033222 A1 | 2/2005 | Haggstrom et al. |
| 2005/0033264 A1 | 2/2005 | Redinger |
| 2005/0054989 A1 | 3/2005 | McGuckin et al. |
| 2005/0055012 A1 | 3/2005 | Trerotola |
| 2005/0059925 A1 | 3/2005 | Maginot et al. |
| 2005/0070842 A1 | 3/2005 | Lotito et al. |
| 2005/0080398 A1 | 4/2005 | Markel et al. |
| 2005/0085765 A1 | 4/2005 | Voorhees |
| 2005/0096585 A1* | 5/2005 | Schon ............... A61M 25/0026 604/43 |
| 2005/0113904 A1* | 5/2005 | Shank ...................... A61F 2/07 623/1.16 |
| 2005/0131341 A1 | 6/2005 | McGuckin et al. |
| 2005/0171469 A1 | 8/2005 | Cunningham |
| 2005/0187535 A1 | 8/2005 | Wilson et al. |
| 2005/0209582 A1 | 9/2005 | Quinn et al. |
| 2005/0215977 A1 | 9/2005 | Uschold |
| 2005/0228339 A1 | 10/2005 | Clark |
| 2005/0245900 A1 | 11/2005 | Ash |
| 2005/0251190 A1 | 11/2005 | McFarlane |
| 2005/0256461 A1 | 11/2005 | DiFiore et al. |
| 2005/0261663 A1 | 11/2005 | Patterson et al. |
| 2005/0267400 A1 | 12/2005 | Haarala et al. |
| 2005/0277862 A1 | 12/2005 | Anand |
| 2005/0283111 A1 | 12/2005 | Maurice |
| 2005/0288623 A1 | 12/2005 | Hjalmarsson |
| 2005/0288706 A1* | 12/2005 | Widomski ......... A61B 17/0057 606/213 |
| 2006/0004316 A1 | 1/2006 | Difiore et al. |
| 2006/0004325 A1 | 1/2006 | Hamatake et al. |
| 2006/0009783 A1 | 1/2006 | Rome et al. |
| 2006/0015072 A1 | 1/2006 | Raulerson |
| 2006/0015130 A1 | 1/2006 | Voorhees et al. |
| 2006/0030827 A1 | 2/2006 | Raulerson et al. |
| 2006/0047267 A1 | 3/2006 | Gately et al. |
| 2006/0047268 A1 | 3/2006 | Stephens |
| 2006/0058775 A1 | 3/2006 | Stevens et al. |
| 2006/0064072 A1 | 3/2006 | Gately et al. |
| 2006/0095062 A1 | 5/2006 | Stephens |
| 2006/0100572 A1 | 5/2006 | DiMatteo et al. |
| 2006/0111537 A1 | 5/2006 | Roby |
| 2006/0161100 A1 | 7/2006 | Hamboly |
| 2006/0184142 A1 | 8/2006 | Schon et al. |

(56) References Cited

U.S. PATENT DOCUMENTS

| | | |
|---|---|---|
| 2006/0189922 A1 | 8/2006 | Amarasinghe et al. |
| 2006/0200111 A1 | 9/2006 | Moehle et al. |
| 2006/0206094 A1 | 9/2006 | Chesnin et al. |
| 2006/0251612 A1 | 11/2006 | Kotzev et al. |
| 2006/0253063 A1 | 11/2006 | Schweikert |
| 2006/0271012 A1 | 11/2006 | Canaud et al. |
| 2007/0005003 A1 | 1/2007 | Patterson et al. |
| 2007/0019181 A1 | 1/2007 | Sinclair et al. |
| 2007/0066964 A1 | 3/2007 | Atkins |
| 2007/0078478 A1 | 4/2007 | Atkins et al. |
| 2007/0106206 A1 | 5/2007 | Appling |
| 2007/0129704 A1 | 6/2007 | O'Mahony et al. |
| 2007/0167925 A1 | 7/2007 | Jacqmein |
| 2007/0191810 A1 | 8/2007 | Kennedy |
| 2007/0225661 A1 | 9/2007 | Ash et al. |
| 2007/0225682 A1 | 9/2007 | Ash et al. |
| 2007/0282274 A1 | 12/2007 | Chesnin |
| 2008/0021417 A1 | 1/2008 | Zawacki et al. |
| 2008/0039774 A1 | 2/2008 | Zawacki et al. |
| 2008/0065029 A1 | 3/2008 | Racz |
| 2008/0082079 A1 | 4/2008 | Braga et al. |
| 2008/0082080 A1 | 4/2008 | Braga |
| 2008/0097409 A1 | 4/2008 | Stephens |
| 2008/0108975 A1* | 5/2008 | Appling ............... A61M 25/003 604/532 |
| 2008/0172012 A1 | 7/2008 | Hiniduma-Lokuge et al. |
| 2008/0214992 A1 | 9/2008 | Haarala et al. |
| 2009/0112153 A1 | 4/2009 | Gregersen et al. |
| 2009/0118661 A1 | 5/2009 | Moehle et al. |
| 2009/0118701 A1 | 5/2009 | Nimkar et al. |
| 2009/0118707 A1 | 5/2009 | Schweikert et al. |
| 2009/0118755 A1 | 5/2009 | Maliglowka et al. |
| 2009/0138034 A1 | 5/2009 | Maliglowka et al. |
| 2009/0157051 A1 | 6/2009 | Appling et al. |
| 2009/0187141 A1 | 7/2009 | Lareau et al. |
| 2009/0192435 A1 | 7/2009 | Gregersen |
| 2009/0204052 A1 | 8/2009 | Nimkar et al. |
| 2009/0204079 A1 | 8/2009 | Nimkar et al. |
| 2009/0204083 A1 | 8/2009 | O'Donnell et al. |
| 2009/0205189 A1 | 8/2009 | Nimkar et al. |
| 2009/0209940 A1 | 8/2009 | Nimkar et al. |
| 2009/0292248 A1 | 11/2009 | Schon et al. |
| 2009/0312687 A1 | 12/2009 | DeFonzo et al. |
| 2010/0081986 A1 | 4/2010 | Matson et al. |
| 2010/0331780 A1 | 12/2010 | Bellisario et al. |
| 2011/0020418 A1 | 1/2011 | Bosley, Jr. et al. |
| 2011/0077672 A1* | 3/2011 | Fleischman ...... A61B 17/00234 606/151 |
| 2011/0301522 A1 | 12/2011 | DeFonzo |
| 2012/0059304 A1 | 3/2012 | Gregersen et al. |
| 2013/0018405 A1 | 1/2013 | Onishi et al. |
| 2013/0079752 A1 | 3/2013 | Gregersen |
| 2013/0253445 A1 | 9/2013 | Nimkar et al. |
| 2014/0018772 A1 | 1/2014 | Ash |
| 2014/0025042 A1 | 1/2014 | Gregersen |
| 2014/0088510 A1 | 3/2014 | Nimkar et al. |
| 2014/0228742 A1 | 8/2014 | Gregersen et al. |
| 2014/0276472 A1 | 9/2014 | VanderStek et al. |
| 2014/0276493 A1* | 9/2014 | Leung ................. A61K 38/39 604/319 |
| 2014/0277052 A1 | 9/2014 | Haselby et al. |
| 2014/0330220 A1 | 11/2014 | Zawacki et al. |
| 2014/0336687 A1 | 11/2014 | Iwase et al. |
| 2015/0073336 A1 | 3/2015 | Moehle et al. |
| 2015/0088100 A1 | 3/2015 | Oborn et al. |

FOREIGN PATENT DOCUMENTS

| | | |
|---|---|---|
| CA | 2474351 A1 | 8/2003 |
| CN | 2788836 Y | 6/2006 |
| CN | 101918067 A | 12/2010 |
| CN | 103170050 A | 6/2013 |
| CN | 101918066 B | 7/2013 |
| DE | 8815869 | 3/1989 |
| DE | 9108132 | 6/1991 |
| DE | 102005051211 A1 | 5/2007 |
| EP | 0030854 A2 | 6/1981 |
| EP | 0132344 A2 | 1/1985 |
| EP | 0301854 | 2/1989 |
| EP | 0332366 A2 | 9/1989 |
| EP | 0332366 A2 | 9/1989 |
| EP | 0386408 A1 | 9/1990 |
| EP | 0453234 | 10/1991 |
| EP | 0476796 A1 | 3/1992 |
| EP | 0495263 A1 | 7/1992 |
| EP | 0650740 A1 | 5/1995 |
| EP | 0711574 A1 | 5/1996 |
| EP | 1471966 A1 | 11/2004 |
| EP | 1599247 A2 | 11/2005 |
| GB | 1503469 | 3/1978 |
| JP | 56-136569 A | 10/1981 |
| JP | 8-510935 T | 11/1996 |
| JP | 2001137350 | 5/2001 |
| JP | 2008500081 A | 1/2008 |
| JP | 4827377 B2 | 11/2011 |
| SU | 459237 A1 | 2/1975 |
| SU | 45923 A | 11/2004 |
| WO | 9108132 A1 | 6/1991 |
| WO | WO-9316741 A1 | 9/1993 |
| WO | WO-9316752 A1 | 9/1993 |
| WO | 9709086 A1 | 3/1997 |
| WO | 9717102 | 5/1997 |
| WO | WO-9722374 A1 | 6/1997 |
| WO | 9737699 | 10/1997 |
| WO | 9904844 A1 | 2/1999 |
| WO | 0023137 A1 | 4/2000 |
| WO | 0218004 A2 | 3/2002 |
| WO | 02058776 A2 | 8/2002 |
| WO | 02083223 A1 | 10/2002 |
| WO | 03030960 A2 | 4/2003 |
| WO | 03033049 A2 | 4/2003 |
| WO | 03066148 A1 | 8/2003 |
| WO | 2004075962 A2 | 9/2004 |
| WO | 2004096334 | 11/2004 |
| WO | 2004112876 | 12/2004 |
| WO | WO-2005018712 A2 | 3/2005 |
| WO | WO-2005023336 A2 | 3/2005 |
| WO | 2005077449 | 8/2005 |
| WO | 2005084741 A1 | 9/2005 |
| WO | 2005118039 A1 | 12/2005 |
| WO | 2006034877 | 4/2006 |
| WO | 2009051967 A1 | 4/2009 |
| WO | 2009055332 A1 | 4/2009 |
| WO | 2009059220 A1 | 5/2009 |
| WO | 2015077560 A1 | 5/2015 |
| WO | 2016/011091 A1 | 1/2016 |

OTHER PUBLICATIONS

Bander, et al., Central Venous Angioaccess for Hemodialysis and Its Complications, Seminars in Dialysis, 1992, vol. 5, No. 2, pp. 121-128.

Baranowski, L., Central Venous Access Devises, Journal of Intravenous Nursing, 1993, vol. 16, No. 3, pp. 167-194.

Believed to be an unpublished sketch of a conception by Dr. John Frusha; date of sketch believed to be Jun. 24, 1997.

Berkoben, et al., Maintenance of Permanent Hemodialysis Vascular Access Patency, ANNA Journal, 1995, vol. 22, No. 1, pp. 17-24.

Bolz, et al., Catheter Malfunction and Thrombus Formation on Double-Lumen Hemodialysis Catheters: An Intravascular Ultrasonographic Study, American Journal of Kidney Diseases, 1995, vol. 25, No. 4, pp. 597-602.

Bour, et al., Experience With the Double Lumen Silastic® Catheter for Hemoaccess Surgery, Gynecology & Obstetrics, 1990, vol. 171, pp. 33-39.

Campbell, et al., Radiological Insertion of Long-term Venous Access Devises, Seminars in Interventional Radiology, 1994, vol. 11, No. 4. pp. 366-375.

Canaud, B. et al., "Permanent Twin Catheter: A Vascular Access Option of Choice for Haemodialysis in Elderly Patients," 13(7):82-88 (1998).

(56) References Cited

OTHER PUBLICATIONS

Claim Construction Order of Federal District Court dated May 9, 2005 in *Thierry Pourchez and Bard Access Systems, Inc. v. Diatek, Inc. and Arrow International, Inc.* litigation (S.D. N.Y. 03 Civ. 0972).
Claim Construction Order of Federal District Court dated Oct. 31, 2006 in *Arrow Int'l. Inc. and Arrow Int'l. Investment Corp. v. Spire Biomedical, Inc.* litigation, (D. Mass. Civil Action No. 06-CV-11564).
Decision of Federal District Court dated Jul. 7, 2009 granting Summary Judgment of Invalidity in *Arrow Int'l. Inc. and Arrow Int'l. Investment Corp. v. Spire Biomedical, Inc.* litigation, (D. Mass. Civil Action No. 06-CV-11564).
Dialysis Vascular Access, Technological Innovations Improving Flow(AngioDynamics Inc.) brochure, 4 pages.
Donaldson, et al., Peripherally Inserted Central Venous Catheters: US-guided Vascular Access in Pediatric Patients1, Radiology, 1995, vol. 197, pp. 542-544.
Dunea, et al., A Survey of Permanent Double Lumen Catheters in Hemodialysis Patients, ASAIO Transac. 1991:37:M276-7.
Dupont et al., "Long-Term Development of Permcath Quinton Catheter" [French] Néphrologie 15: 105-10 (1994).
Gallichio, et al., Placement of a Double Lumen Silastic Catheter for Hemodialysis Access Through the Cephalic Vein, Journal of the American College of Surgeons, 1994, vol. 179, pp. 171-172.
Gravenstein, et al., In Vitro Evaluation of Relative Perforating Potential of Central Venous Catheters: Comparison of Materials, Selected Models, Number of Lumens, and Angles of Incidence to Simulated Membrane, Journal of Clinical Monitoring, 1991, vol. 7, pp. 1-6.
Haindl, H., Technical complications for port-catheter systems, Reg. Cancer Treat, 1989, 2:238-242.
Haire, et at., Thrombotic Complications of Subclavian Apheresis catheters in Cancer Patients: Prevention With Heparin Infusion, Journal of Clinical Apheresis, 1990, vol. 5, pp. 188-191.
Hull, et al., The Groshong Catheter: Initial Experience and Early Results of Imaging-guided Placement1, Radiology, 1992, vol. 185, pp. 803-807.
Ignotus, et al., Review of Radiological Insertion of Indwelling Central Venous Catheters, minimally invasive Therapy, 1992, 1:373-388.
Instructions for Use (Copyright Dated 1990) for Polycath Polyurethance Central Venous Catheter; believed to have been packaged with product believed to have been sold in the United States before Jan. 2000 and related marketing materials.
Instructions for Use (Copyright Dated 1992) for FloLock Single Lumen Bi-directional Valved Catheter; believed to have been packaged with product believed to have been sold in the United States before Jan. 2000.
Instructions for Use (not dated) for Infuse-a-Cath Polyurethance Central Venous Catheter; believed to have been packaged with product believed to have been sold in the United States before Jan. 2000.
Instructions for Use for Diatek Cannon Catheter Product First Sold in the United States Sep. 2001.
Jones, et al., Efficacy of the Supraclavicular Route for Temporary Hemodialysis Access, Southern Medical Journal, 1992, vol. 85, No. 7, pp. 725-726.
Kaupke, et al., Perforation of the Superior Vena Cava by a Subclavin Hemodialysis Catheter: early detection by angiography, The International Journal of Artificial Organs, 1992, vol. 15, No. 11, pp. 666-668.
Kelber, et al., Factors Affecting Delivery of High-Efficiency Dialysis Using Temporary Vascular Access, American Journal of Kidney Diseases, 1993, vol. 22, No. 1, pp. 24-29.
Lumsden, et al., Hemodialysis Access in the Pediatric Patient Population, The American Journal of Surgery, 1994, vol. 168, pp. 197-201.

Lund, "Percutaneous Translumber Inferior Vena Cava Cannulation and other Alternative Vascular Access Techniques" in Venous Interventional Radiology with Clinical Perspectives, Savader et al, eds, pp. 251-61 (date unknown).
Lund, et al., Percutaneous Translumber Inferior Vena Cava Cannulation for Hemodialysis, American Journal of Kidney Diseases, 1995, vol. 25, No. 5, pp. 732-737.
Maki, D., Pathogenesis, Prevention, and Management of Infections Due to Intravascular Devices Used for Infusion Therapy, in Infections Associated with Indwelling Medical Devices, Bisno et al, eds, American Society for Microbiology, 1989, pp. 161-177.
Mauro, et al., Radiologic Placement of Long-term Central Venous Catheters: A Review, JVIR, 1993, vol. 4, No. 1, pp. 127-137.
McGee, et al., Accurate placement of central venous catheters: A prospective, randomized, multicenter trial, Critical Care Medicine, 1993, vol. 21, No. 8, pp. 1118-1123.
Medcomp, "For Access via the Internal Jugular Vein . . . The Medcomp TESIO Catheter is the Solution: The Short and Long Term Solution to Subclavian Venin Stenosis and Difficult Access Problems"-Brochure, 4 pp.
Moss, et al., Use of a Silicone Catheter With a Dacron Cuff for Dialysis Short-Term Vascular Access, American Journal of Kidney Diseases, 1988, vol. XII, No. 6, pp. 492-498.
Northsea, C., Using Urokinase to Restore Patency in Double Lumen Catheters, ANNA Journal 1994, vol. 21, No. 5, pp. 261-273.
Parsa, et al., Establishment of Intravenous Lines for Long-term Intravenous Therapy and Monitoring, Surgical Clinics of N. Am. 1985, vol. 65, No. 4, pp. 835-865.
Parsa, et al., Vascular Access Techniques, Monitoring, pp. 122-145 (date unknown).
Pasquale, et al., Groshong® versus Hickman® Catheters, Surgery, Gynecology & Obstetrics, 1992, vol. 174, pp. 408-410.
Passaro, et al., Long-term Silastic Catheters and Chest Pain, Journal of Parenteral andEnteral Nutrition, 1994, vol. 18, Bo. 3, pp. 240-242.
Paulsen, et al., Use of Tissue Plasminogen Activator for Reopening of Clotted Dialysis Catheters, Nephron, 1993, vol. 64, pp. 468-470.
Picture of device believed to be partial sample of a product believed to have been sold in the United States with the Polycath and/or Infuse-a-Cath Instructions for Use, 1 page.
Raaf, et al., Open Insertion of Right Atrial Catheters Through the Jugular Veins, surgery, Gynecology & Obstetrics, 1993, vol. 177, pp. 295-298.
Schwab, et al., Prospective Evaluation of a Dacron Cuffed Hemodialysis Catheter for Prolonged Use, American Journal of Kidney Diseases, 1998, vol. XI, No. 2, pp. 166-169.
Schwab, et al., Vascular Access: Case Oriented Discussions of Selected Critical Issues: Hemodialysis Catheters for Permanent Use (date unknown).
Shaffer D., lessons from Vascular Access Procedures for Hemodialysis, Surgical Oncology Clinics of North America, 1995, vol. 4, No. 3, pp. 537-549.
Shaffer, D., Catheter-Related Sepsis Complication Long-Term Tunnelled Central Venous Dialysis Catheters: Management by Guidewire Exchange, American Journal of Kidney Disease, 1995, vol. 25, No. 4. pp. 593-596.
Sioshansi, P., New Processes for Surface Treatment of Catheters, Artificial Organs, 1994, 18(4):266-271.
Swartz, et al., Successful Use of Cuffed Central venous Hemodialysis Catheters Inserted Percutaneously, J. Am. Soc. Nephrol., 1994, 4:1719-1725.
Tesio, et al., Double Catherization of the Internal Jugular Vein for Hemodialysis: Indications, Techniques, and Clinical Results, Artificial Organs, 1994, vol. 18, No. 4, pp. 301-304.
Treiman, et al., Chronic Venous Access in Patients with Cancer, Cancer, 1993, vol. 72, No. 3, pp. 760-765.
Twadorski, et al., "Blood Recirculation in Intravenous Catheters for Hemodialysis" J. am. Soc. Nephrol. 3:1978-81 (1993).
Uldall, P. Subclavian Cannulation Is No longer Necessary or justified in Patients with End-Stage Renal failure, Seminar in Dialysis, 1994, vol. 7, No. 3, pp. 161-164.

(56) References Cited

OTHER PUBLICATIONS

Wechsler, et al., Thrombosis and Infection Caused by Thoracic Venous Catheters: Pathogenesis and Imagings Findings, AJR, 1993; 160:467-471.
Weitzel, et al., Successful use if Indwelling Cuffed Femoral Vein Catheters in Ambulatory Hemodialysis Patients, America Journal of Kidney diseases, 1993, vol. 22, No. 3, pp. 426-429.
U.S. Appl. No. 10/842,586, filed May 10, 2004 Non-Final Office Action dated Nov. 13, 2008.
U.S. Appl. No. 10/842,586, filed May 10, 2004 Non-Final Office Action dated Nov. 23, 2009.
U.S. Appl. No. 10/874,298, filed Jun. 9, 2004 Advisory Action dated Feb. 19, 2009.
U.S. Appl. No. 10/874,298, filed Jun. 9, 2004 Final Office Action dated Jul. 15, 2008.
U.S. Appl. No. 10/874,298, filed Jun. 9, 2004 Final Office Action dated Jul. 7, 2010.
U.S. Appl. No. 10/874,298, filed Jun. 9, 2004 Final Office Action dated Mar. 18, 2014.
U.S. Appl. No. 10/874,298, filed Jun. 9, 2004 Non-Final Office Action dated Aug. 1, 2013.
U.S. Appl. No. 10/874,298, filed Jun. 9, 2004 Non-Final Office Action dated Aug. 18, 2011.
U.S. Appl. No. 10/874,298, filed Jun. 9, 2004 Non-Final Office Action dated Dec. 30, 2009.
U.S. Appl. No. 10/874,298, filed Jun. 9, 2004 Non-Final Office Action dated Feb. 2, 2011.
U.S. Appl. No. 10/874,298, filed Jun. 9, 2004 Non-Final Office Action dated Jul. 23, 2009.
U.S. Appl. No. 10/874,298, filed Jun. 9, 2004 Non-Final Office Action dated Jul. 9, 2014.
U.S. Appl. No. 10/874,298, filed Jun. 9, 2004 Non-Final Office Action dated May 23, 2006.
U.S. Appl. No. 10/874,298, filed Jun. 9, 2004 Non-Final Office Action dated May 24, 2007.
U.S. Appl. No. 11/859,106, filed Sep. 21, 2007 Final Office Action dated Sep. 1, 2009.
U.S. Appl. No. 11/859,106, filed Sep. 21, 2007 Non-Final Office Action dated Feb. 5, 2009.
U.S. Appl. No. 11/859,106, filed Sep. 21, 2007 Non-Final Office Action dated Mar. 30, 2011.
U.S. Appl. No. 11/859,106, filed Sep. 21, 2007 Non-Final Office Action dated Jun. 25, 2008.
U.S. Appl. No. 11/874,447, filed Oct. 18, 2007 Decision on Appeal dated Dec. 26, 2012.
U.S. Appl. No. 11/874,447, filed Oct. 18, 2007 Examiner's Answer dated Apr. 28, 2010.
U.S. Appl. No. 11/874,447, filed Oct. 18, 2007 Final Office Action dated Jul. 22, 2009.
U.S. Appl. No. 11/874,447, filed Oct. 18, 2007 Non-Final Office Action dated Jan. 6, 2009.
U.S. Appl. No. 11/874,447, filed Oct. 18, 2007 Non-Final Office Action dated Jul. 12, 2013.
U.S. Appl. No. 11/874,447, filed Oct. 18, 2007 Non-Final Office Action dated Jul. 9, 2008.
U.S. Appl. No. 11/874,447, filed Oct. 18, 2007 Notice of Allowance dated Apr. 18, 2014.
U.S. Appl. No. 12/244,514, filed Oct. 2, 2008 Final Office Action dated Jun. 19, 2012.
U.S. Appl. No. 12/244,514, filed Oct. 2, 2008 Non-Final Office Action dated Jan. 17, 2012.
U.S. Appl. No. 12/244,559, filed Oct. 2, 2008 Examiner's Answer dated Mar. 27, 2013.
U.S. Appl. No. 12/244,559, filed Oct. 2, 2009 Final Office Action dated Jul. 3, 2012.
U.S. Appl. No. 12/244,559, filed Oct. 2, 2009 Non-Final Office Action dated Mar. 14, 2012.
U.S. Appl. No. 12/244,514, filed Oct. 2, 2008 Advisory Action dated Sep. 5, 2012.
U.S. Appl. No. 12/244,514, filed Oct. 2, 2008 Final Office Action dated Jul. 11, 2011.
U.S. Appl. No. 12/244,514, filed Oct. 2, 2008 Non-Final Office Action dated Jan. 19, 2011.
U.S. Appl. No. 12/244,544, filed Oct. 2, 2008 Final Office Action dated Jul. 11, 2011.
U.S. Appl. No. 12/244,544, filed Oct. 2, 2008 Non-Final Office Action dated Dec. 22, 2010.
U.S. Appl. No. 12/244,554, filed Oct. 2, 2008 Final Office Action dated Dec. 27, 2010.
U.S. Appl. No. 12/244,554, filed Oct. 2, 2008 Non-Final Office Action dated Jul. 6, 2010.
U.S. Appl. No. 12/253,870, filed Oct. 17, 2008 Non-Final Office Action dated Jan. 21, 2011.
U.S. Appl. No. 12/253,870, filed Oct. 17, 2008 Notice of Allowance dated Aug. 19, 2011.
U.S. Appl. No. 12/262,820, filed Oct. 31, 2008 Non-Final Office Action dated Feb. 18, 2011.
U.S. Appl. No. 12/262,820, filed Oct. 31, 2008 Notice of Allowance dated Sep. 28, 2011.
U.S. Appl. No. 12/263,141, filed Oct. 31, 2008 Advisory Action dated Aug. 17, 2011.
U.S. Appl. No. 12/263,141, filed Oct. 31, 2008 Final Office Action dated May 26, 2011.
U.S. Appl. No. 12/263,141, filed Oct. 31, 2008 Non-Final Office Action dated Jan. 5, 2011.
U.S. Appl. No. 12/414,467, filed Mar. 30, 2009 Final Office Action dated Feb. 7, 2012.
U.S. Appl. No. 12/414,467, filed Mar. 30, 2009 Notice of Allowance dated May 31, 2012.
U.S. Appl. No. 12/414,467, filed Mar. 30, 2009 Non-Final Office Action dated Aug. 11, 2011.
U.S. Appl. No. 13/294,941, filed Nov. 11, 2011 Non-Final Office Action dated May 31, 2013.
U.S. Appl. No. 13/294,941, filed Nov. 11, 2011 Notice of Allowance dated Nov. 27, 2013.
U.S. Appl. No. 13/329,159, filed Dec. 16, 2011 Non-Final Office Action dated May 16, 2014.
U.S. Appl. No. 13/445,713, filed Apr. 12, 2012 Advisory Action dated Aug. 8, 2013.
U.S. Appl. No. 13/445,713, filed Apr. 12, 2012 Final Office Action dated May 30, 2013.
U.S. Appl. No. 13/445,713, filed Apr. 12, 2012 Non-Final Office Action dated Jan. 2, 2013.
U.S. Appl. No. 13/445,713, filed Apr. 12, 2012 Notice of Allowance dated Oct. 18, 2013.
U.S. Appl. No. 13/897,292, filed May 17, 2013 Final Office Action dated Apr. 9, 2015.
U.S. Appl. No. 13/897,292, filed May 17, 2013 Non-Final Office Action dated Nov. 20, 2014.
U.S. Appl. No. 14/032,858, filed Sep. 20, 2013 Final Office Action dated Mar. 31, 2015.
U.S. Appl. No. 14/032,858, filed Sep. 20, 2013 Non-Final Office Action dated Nov. 4, 2014.
U.S. Appl. No. 14/252,567, filed Apr. 14, 2014 Non-Final Office Action dated Mar. 31, 2015.
U.S. Appl. No. 14/328,541, filed Jul. 10, 2014 Non-Final Office Action dated Apr. 9, 2015.
US Patent File History U.S. Pat. No. 5,403,291 (Abrahamson), issued Apr. 4, 1995.
US Patent File History U.S. Pat. No. 5,489,278 (Abrahamson), issued Feb. 6, 1996.
US Patent File History U.S. Pat. No. 5,685,867 (Twardowski et al.), issued Nov. 11, 1997.
*Arrow International, Inc. et al* v. *Spire Biomedical, Inc.*, U.S. Dist Ct Dist MA CA No. 06-CV-11564-DPW, Declaration of Dr. Karim Valji (Jul. 17, 2008).
*Arrow International, Inc. et al* v. *Spire Biomedical, Inc.*, U.S. Dist Ct Dist MA CA No. 06-CV-11564-DPW, Declaration of Kenneth Todd Cassidy (Jul. 16, 2008).
*Arrow International, Inc. et al* v. *Spire Biomedical, Inc.*, U.S. Dist Ct Dist MA CA No. 06-CV-11564-DPW, Declaration of Rebecca R.

(56) References Cited

OTHER PUBLICATIONS

Eisenberg in Opposition to Defendant's Motion for Partial Summary Judgment of Invalidity (Jun. 8, 2009).
*Arrow International, Inc. et al v. Spire Biomedical, Inc.*, U.S. Dist Ct Dist MA CA No. 06-CV-11564-DPW, Memorandum of Law in Support of Defendant's Motion for Summary Judgment on Invalidity [Redacted Pursuant to Jun. 10, 2008 Order on Motion to Seal].
*Arrow International, Inc. et al v. Spire Biomedical, Inc.*, U.S. Dist Ct Dist MA CA No. 06-CV-11564-DPW, Memorandum of Law in Support of Defendant's Motion for Summary Judgment on Invalidity Exhibit A (Jul. 10, 2009).
*Arrow International, Inc. et al v. Spire Biomedical, Inc.*, U.S. Dist Ct Dist MA CA No. 06-CV-11564-DPW, Plaintiff's Memorandum in Opposition to Defendant's Motion for Summary Judgement on Non-Infringement (Jul. 17, 2008).
*Arrow International, Inc. et al. v. Spire Biomedical, Inc.*, U.S. Dist. Ct. Dist. MA CA No. 06-CV-11564-DPW, Defendant's Omnibus Statement of Material Facts in Support of its Motions for Summary Judgment (Jun. 10, 2008) [Redacted Pursuant to Jun. 10, 2008 Order on Motion to Seal].
Bard Access Systems Hickman®, Leonard®, and Broviac® Central Venous Catheters (Long Term), Instructions for Use, 31 pages, 1999.
Bard Access Systems Hickman®, Leonard®, and Broviac® Central Venous Catheters, Nursing Procedural Manual, 52 pages, Jun. 1994.
BARD Davol® Hickman® Round Dual Lumen Catheters for Central Venous Access Informational Brochure, 4 pages, 1994.
BARD Hickman® Catheters Informational Brochure, 3 pages, 1994.
CAMP, "Care of the Groshong Catheter", Oncol Nurs Forum, vol. 15, No. 6, 1988.
CN 200880121182.0 filed Oct. 20, 2008 First Office Action dated May 2, 2012.
CN 200880121183.5 filed Oct. 2, 2008 First Office Action dated Mar. 28, 2012.
CN 200880121183.5 filed Oct. 2, 2008 Second Office Action dated Aug. 17, 2012.
CN 200880121183.5 filed Oct. 2, 2008 Third Office Action dated Dec. 11, 2012.
CN 200880123095.9 filed Oct. 20, 2008 First Office Action dated Feb. 13, 2012.
CN 200880123095.9 filed Oct. 20, 2008 Second Office Action dated Dec. 18, 2012.
CN 200880123533.1 filed Jun. 30, 2008 First Office Action dated May 28, 2012.
CN 200880123533.1 filed Jun. 30, 2008 Notice of Grant dated Dec. 24, 2012.
CN 201310073124.8 filed Mar. 7, 2013 First Office Action dated May 5, 2014.
Declaration of Gregory S. Haas (Plaintiff's Exhibit 88 in Haas Deposition), Mar. 13, 2003, *Thierry Pourchez and Bard Access Systems, Inc. v. Diatek, Inc. and Arrow International, Inc.*, Civil Action No. 03-CV-0972 (S.D.N.Y.).
Defendant's Exhibits DX78-DX114, *Thierry Pourchez and Bard Access Systems, Inc. v. Diatek, Inc. and Arrow International, Inc.*, Civil Action No. 03-CV-0972 (S.D.N.Y.), 2003.
Defendants' Reponses and Objections to Plaintiffs' Second Set of Interrogatories (Excerpt), *Thierry Pourchez and Bard Access Systems, Inc. v. Diatek, Inc. and Arrow International, Inc.*, Civil Action No. 03-CV-0972 (S.D.N.Y.) (Oct. 8, 2003).
Delmore et al., "Experience with the Groshong Long-Term Central Venous Catheter", Gynecologic Oncology 34, 216-218 (1989).
Dialysis Vascular Access, SchonXL® Temporary Dialysis (AngioDynamics Inc.) brochure, Nov. 1998.
Difiore, "Central Venous Dialysis Catheter Evaluatio in Swine", Journal of Vascular Access Devices, Fall 2000.
Dupont et al, Long-term development of Permacath Quinton catheters used as a vascular access route for extra-renal detoxification; Néphrologie, vol. 15, pp. 105-110, 1994.

EP 04712925.9 filed Feb. 19, 2004 Office Action dated Nov. 7, 2008.
EP 08839196.6 filed Oct. 2, 2008 Examination Report dated Jan. 16, 2013.
EP 08839196.6 filed Oct. 2, 2008 Search Opinion dated Jul. 12, 2011.
EP 08839196.6 filed Oct. 2, 2008 Search Report dated Jul. 12, 2011.
EP 08872340.8 filed Oct. 2, 2008 Extended European Search Report and an Opinion dated Apr. 19, 2012.
JP 2010-532299 filed Apr. 30, 2010 Final Notice of Reason for Rejection dated Feb. 8, 2013.
JP 2010-532299 filed Apr. 30, 2010 Official Action dated Apr. 23, 2012.
JP App. No. 2003-565569 filed Feb. 7, 2003, Translated Decision of Refusal mailed Dec. 24, 2009.
JP App. No. 2003-565569 filed Feb. 7, 2003, Translated Official Action mailed May 28, 2009.
JP App. No. 2003-565569 filed Feb. 7, 2003, Translated Official Action mailed Nov. 7, 2008.
Kapoian et al. Dialysis as Treatment of End-Stage Renal Disease, Chapter 5: Dialysis Access and Recirculation, © 1999.
Malviya et al., "Vascular Access in Gynecological Cancer Using the Groshong Right Atrial Catheter", Gynecological Oncology 33, 313-316 (1989).
Medcomp® Brochure, "Ash Split Cath™XL", Dec. 2001, PN 2291.
Medcomp® Brochure, "Ash Split Cath™", Guidewire Weave Insertion Technique, Jan. 2002, PN 2296.
Medcomp® Brochure, "Ash Split Cath™", Jul. 2001, PN 2114.
Medcomp® Brochure, "Ash Split Cath™", Nov. 1997, PN 2050.
Medcomp® Brochure, "Ash Split Cath® II", Aug. 2002, PN 2334.
Medcomp® Brochure, "Magna™ High Flow Catheter", Mar. 2002, PN 2321.
Moss et al, Use of Silicone Dual-Lumen Catheter with a Dacron Cuff as a Long Term Vascular Access for Hemodialysis Patients, Amer J Kidney Diseases, vol. XVI, No. 3, pp. 211-215, Sep. 1990.
Myers, R.D. et al, New Double-lumen Polyethylene Cannula for Push-pull Perfusion of Brain Tissue in Vivo, Journal of Neuroscience Methods, pp. 205-218, vol. 12, 1985.
OriGen, OriGen Biomedical Dual Lumen Catheter, from <http://origen.net/catheter.html>, downloaded May 13, 2009, 4 pages (reprinted for submission on Jul. 21, 2011).
Patel et al., "Sheathless Technique of Ash Split-Cath Insertion", 12 JVIR 376-78 (Mar. 2001).
PCT/US2003/003751 filed Feb. 7, 2003 Preliminary Examination Report dated May 5, 2004.
PCT/US2003/003751 filed Feb. 7, 2003 Search Report dated Jul. 3, 2003.
PCT/US2004/005102 filed Feb. 19, 2004 Preliminary Report Patenability dated Aug. 29, 2005.
PCT/US2004/005102 filed Feb. 19, 2004 Search Report dated Dec. 27, 2004.
PCT/US2004/005102 filed Feb. 19, 2004 Written Opinion dated Aug. 21, 2005.
PCT/US2008/078551 filed Oct. 2, 2008 International Preliminary Report on Patentability dated Apr. 20, 2010.
PCT/US2008/078551 filed Oct. 2, 2008 Search Report dated Mar. 13, 2009.
PCT/US2008/078551 filed Oct. 2, 2008 Written Opinion dated Mar. 13, 2009.
PCT/US2008/078560 filed Oct. 2, 2008 Preliminary Report on Patentability dated Aug. 26, 2010.
PCT/US2008/078560 filed Oct. 2, 2008 Search Report dated Mar. 16, 2009.
PCT/US2008/078560 filed Oct. 2, 2008 Written Opinion dated Mar. 16, 2009.
PCT/US2008/078566 filed Oct. 2, 2008 International Preliminary Report on Patentability dated Apr. 20, 2010.
PCT/US2008/078566 filed Oct. 2, 2008 Search Report dated Mar. 19, 2009.
PCT/US2008/078566 filed Oct. 2, 2008 Written Opinion dated Mar. 19, 2009.
PCT/US2008/078571 filed Oct. 2, 2008 Preliminary Report on Patentability dated Aug. 26, 2010.

(56) References Cited

OTHER PUBLICATIONS

PCT/US2008/078571 filed Oct. 2, 2008 Search Report dated Mar. 20, 2009.
PCT/US2008/078571 filed Oct. 2, 2008 Written Opinion dated Mar. 20, 2009.
PCT/US2008/080463 filed Oct. 20, 2008 Preliminary Report on Patentability dated Apr. 27, 2010.
PCT/US2008/080463 filed Oct. 20, 2008 Search Report dated Mar. 16, 2009.
PCT/US2008/080463 filed Oct. 20, 2008 Written Opinion dated Apr. 16, 2009.
PCT/US2008/082106 filed Oct. 31, 2008 International Preliminary Report on Patentability dated May 4, 2010.
PCT/US2008/082106 filed Oct. 31, 2008 Search Report dated Jan. 12, 2009.
PCT/US2008/082106 filed Oct. 31, 2008 Written Opinion dated Jan. 12, 2009.
PCT/US2014/066811 filed Nov. 21, 2014 International Search Report and Written Opinion dated Apr. 15, 2015.
QUINTON® Catheter Products (1993).
Raaf Dual Lumen Right Atrial Catheters Brochure—Quinton Instrument Co., 6 pages, 1993.
Rawn, et al., The Hemodialysis Access, Chapter 9, pp. 9.1-9.11, available at <<http://msl1.mit.edu/ESD10/kidneys/HndbkPDF/Chap09.pdf>>, last accessed Jun. 4, 2012.
Septum, Wikipedia, The Free Encyclopedia, hhttp://en.wikipedia.org/wiki/Septum (last visited Dec. 18, 2012) (defining "septum" as "a wall, dividing a cavity or structure into smaller ones").
Taber's Cyclopedic Medical Dictionary 1662 (16th ed. 1989) (defining "septum" as a "wall dividing two cavities").
Tal, Michael G, Comparison of Recirculation Percentage of the Palindrome Catheter and Standard Hemodialysis Catheters in a Swine Model, J Vasc Interv Radiol, pp. 1237-1240, vol. 16, No. 9, 2005.
The Groshong™ Peripherally Inserted Central Venous Catheter Brochure—Cath-tech®, 4 pages, 1988.
Transcript of Videotaped Deposition of Gregory Haas (Excerpt), Sep. 23, 2003, *Thierry Pourchez and Bard Access Systems, Inc. v. Diatek, Inc. and Arrow International, Inc.*, Civil Action No. 03-CV-0972 (S.D.N.Y).
Transcript of Videotaped Deposition of Thierry Pourchez, vol. 1, Oct. 16, 2003, *Thierry Pourchez and Bard Access Systems, Inc. v. Diatek, Inc. and Arrow International, Inc.*, Civil Action No. 03-CV-0972 (S.D.N.Y).
Transcript of Videotaped Deposition of Thierry Pourchez, vol. 2, Oct. 17, 2003, *Thierry Pourchez and Bard Access Systems, Inc. v. Diatek, Inc. and Arrow International, Inc.*, Civil Action No. 03-CV-0972 (S.D.N.Y).
Twardowski et al. "Side Holes at the Tip of Chronic Hemodialysis Catehters are Harmful," The Journal of Vascular Access 2001; 2:8-16.
TYCO Healthcare, Mahurkar Dual Lumen Catheters, Informational Brochure, 2 pages, 2004.
TYCO Healthcare, Mahurkar QPlus High Flow Acute Care Catheter, Informational Brochure, 2 pages, 2004.
TYCO Healthcare, Tal Palindrome™ Dual Lumen Catheters Order Information, Features and Benefits, Frequently Asked Questions, printed from http://www.kendallvasculartherapy.com/VascularTherapy, 6 pages, on Mar. 1, 2007.
U.S. Appl. No. 10/371,774, filed Feb. 21, 2003 Final Office Action dated Jan. 19, 2007.
U.S. Appl. No. 10/371,774, filed Feb. 21, 2003 Final Office Action dated Mar. 7, 2007.
U.S. Appl. No. 10/371,774, filed Feb. 21, 2003 Non-Final Office Action dated Jul. 17, 2006.
U.S. Appl. No. 10/371,774, filed Feb. 21, 2003 Notice of Allowance dated Jun. 1, 2007.
U.S. Appl. No. 10/445,731, filed May 27, 2003 Non-Final Office Action dated Apr. 13, 2007.
U.S. Appl. No. 10/445,731, filed May 27, 2003 Non-Final Office Action dated Dec. 12, 2008.
U.S. Appl. No. 10/445,731, filed May 27, 2003 Non-Final Office Action dated May 30, 2008.
U.S. Appl. No. 10/842,586, filed May 10, 2004 Advisory Action dated Oct. 9, 2008.
U.S. Appl. No. 10/842,586, filed May 10, 2004 Final Office Action dated Jul. 29, 2008.
U.S. Appl. No. 10/842,586, filed May 10, 2004 Final Office Action dated May 25, 2010.
U.S. Appl. No. 10/842,586, filed May 10, 2004 Non-Final Office Action dated Jan. 7, 2008.
U.S. Appl. No. 10/842,586, filed May 10, 2004 Non-Final Office Action dated Jun. 16, 2009.
Lubrizol, "Lubrizol's Family of TPUs" Brochure (2005), 9 pages.
U.S. Appl. No. 12/244,559, filed Oct. 2, 2008 Decision on Appeal dated Aug. 31, 2015.
U.S. Appl. No. 14/032,858, filed Sep. 20, 2013, Notice of Allowance dated Jun. 26, 2015.
U.S. Appl. No. 14/252,567, filed Apr. 14, 2014 Notice of Allowance dated Sep. 3, 2015.
U.S. Appl. No. 14/328,541, filed Jul. 10, 2014 Final Office Action dated Oct. 22, 2015.
PCT/US15/40463 filed Jul. 14, 2015 International Search Report and Written Opinion dated Dec. 18, 2015.
U.S. Appl. No. 14/094,534, filed Dec. 2, 2013 Non-Final Office Action dated Feb. 24, 2016.
U.S. Appl. No. 14/542,495, filed Nov. 14, 2014 Non-Final Office Action dated May 10, 2016.
U.S. Appl. No. 13/294,941, filed Nov. 11, 2011 Non-Final Office Action dated May 27, 2016.
U.S. Appl. No. 14/094,534, filed Dec. 2, 2013 Final Office Action dated Jul. 20, 2016.
U.S. Appl. No. 14/094,534, filed Dec. 2, 2013 Notice of Allowance dated Sep. 30, 2016.
U.S. Appl. No. 14/542,495, filed Nov. 14, 2014 Final Office Action dated Aug. 31, 2016.
U.S. Appl. No. 14/675,236, filed Mar. 31, 2015 Non-Final Office Action dated Feb. 2, 2017.

\* cited by examiner

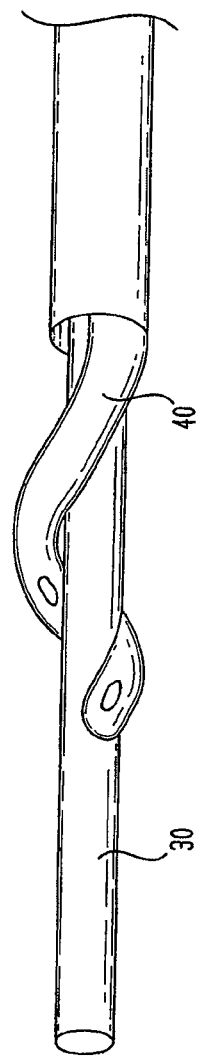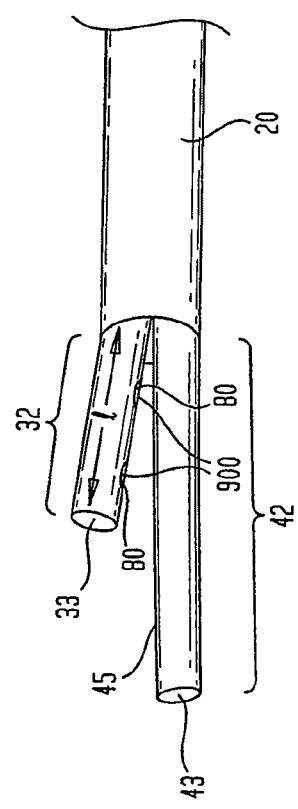
FIG. 5C
FIG. 6A

SPLITABLE TIP CATHETER WITH BIORESORBABLE ADHESIVE

CROSS-REFERENCE TO RELATED APPLICATIONS

This application is a divisional of U.S. patent application Ser. No. 10/874,298 filed on Jun. 9, 2004 now U.S. Pat. No. 8,992,454, and entitled "Splitable Tip Catheter With Bioresorbable Adhesive," which is hereby incorporated by reference in its entirety.

FIELD OF THE INVENTION

The present invention generally relates to catheters and preferably to multi-lumen catheters used for vascular access.

BACKGROUND OF THE INVENTION

Multi-lumen catheters and, in particular split-tip catheters, are desirable for various treatment applications such as hemodialysis where fluid extraction and infusion occur simultaneously. Hemodialysis is the separation of metabolic waste products and water from the blood by diffusion through a semipermeable membrane. Typically, a hemodialysis unit is connected to a patient's body by a catheter. The catheter's distal end is placed in a blood vessel and its proximal end is connected to a hemodialysis unit.

During hemodialysis, a patient's blood flows through a double lumen catheter to the hemodialysis unit which provides filtration and controls the flow of blood. A double lumen catheter has two lumens that independently allow fluid extraction and return. For example, one lumen can be used for removing blood from a patient for processing in the hemodialysis machine and the other lumen can be used for subsequently returning the processed blood back to the patient's circulatory system.

Parameters that can be varied to achieve adequate hemodialysis include blood flow rate, dialysis solution flow rate, dialyzer competency, and temperature. Generally, raising the blood flow rate increases dialyzer clearance of small molecular weight solutes. Consequently, higher blood flow rates have been used to improve dialysis clearance efficiency. However, conditions such as access recirculation decrease clearance. Access recirculation is the recirculation of treated blood back into the hemodialysis unit causing inadequate dialysis. This problem effectively reduces blood flow rates thereby diminishing the efficiency of the hemodialysis process causing the duration of the treatment needed for dialysis to increase. Access recirculation can be particularly of concern when using a double lumen catheter due to the close proximity of the intake and outflow ports at the distal tip of the catheter.

Various double lumen catheter designs have been suggested for the purpose of reducing access recirculation. The distal ends of intake and outflow lumens have been longitudinally spaced 20-30 mm apart to prevent recirculation. For example, Twardowski et al. U.S. Pat. No. 5,569,182 discloses that the lumen for return of blood back into the vein should terminate beyond the extraction lumen. The purpose of this is to prevent cleansed blood, exiting from the outlet point of the catheter, from re-entering the catheter's blood inlet point and returning to the dialysis machine. However, certain disadvantages have been noted by such large longitudinal spacing between the distal ends of the respective lumens. For example, blood flow stagnation in the region of the blood vessel between two widely separated tips can lead to clot formation.

In addition to longitudinal spacing of the distal openings of the lumens for blood extraction and return, others have suggested that the distal end of a multi-lumen catheter can be split such that the distal tips of the lumens can independently move in the blood vessel to optimize the fluid dynamics of the different functions (blood extraction and blood return).

In general, good catheter outcomes depend on proper positioning of the catheter in the blood vessel. Insertion complications include pneumothorax, hemothorax, and cardiac tamponade, as well as poor blood flow rates, poor clearances, and long-term complications such as catheter dysfunction and fibrin sheath formation. These complications are compounded by the use of double lumen catheters because of their size.

Additional difficulties can be encountered when split distal tips must be inserted into a blood vessel. Typical insertion techniques of conventional double lumen catheters require the use of a peel-away sheath over a guidewire. Frequently there is a preference to insert the catheters without the use of a peel-away sheath to eliminate the risk of an air embolism by the use of two guidewires, or alternatively, inserting the guidewire through the one lumen and threading it through the side hole channels of the other lumen thus utilizing one guidewire, referred to as the "weave technique". Moreover, precise positioning of a multi-lumen catheter can be challenging because the exact placement of the tips can not be assured. An improperly positioned multi-lumen catheter can further result in sub-optimal functionality requiring intervention.

Thus, there remains a need for a multi-lumen catheter that addresses the problems of access recirculation yet retains the comparative ease of insertion of a single lumen catheter.

SUMMARY OF THE INVENTION

Splitable-tip catheters are disclosed having tip elements that are joined with biodegradable or biosoluble adhesive to facilitate insertion and yet provide spatial separation of distal tip elements during use. The invention can be particularly useful in hemodialysis applications where it is desirable to separate blood extraction and return lumens. The adhesive facilitates insertion of the distal end of the catheter as an assembly, e.g., into a blood vessel using a single guidewire, while the biodegradable or biosoluble nature of the adhesive allows the tip elements to separate in vivo. The term "bioresorbable" as used herein encompasses both biodegradable and biosoluble materials.

The biodegradable adhesive, applied to the contacting surfaces of the distal tips of the extraction and return lumens, can be formed from various polymer or copolymer compositions. Additionally, the adhesive can be composed such that the time in which the adhesive biodegrades or biodisolves can be in the range of about 1 second to 1 hour. More generally, the adhesives of the present invention can bioresorb from about 1 second to about 7 days, or from about 1 second to about 1 day, or from about 1 second to about 1 hour, or from about 1 second to about 10 minutes, or from about 10 seconds to about 5 minutes. In another embodiment a splitable tip catheter is disclosed having distal fluid openings to accelerate dissolution. The biodegradable or biosoluble adhesive can be water soluble such that the introduction of saline or similar type fluid will dissolve the adhesive and facilitate the separation of the distal tip elements.

An embodiment of the present invention provides a multi-lumen catheter device for hemodialysis having an elongate catheter body with at least one blood extraction lumen and one blood return lumen extending longitudinally therethrough. The proximal end of the instrument can be adapted for coupling to a hemodialysis apparatus and the distal end terminates in separable distal tip portions adapted for insertion into a blood vessel. The distal end of the catheter includes a distal extraction tip portion for fluid coupling of the extraction lumen with the blood vessel and a distal return tip portion for fluid coupling of the return lumen with the blood vessel, such that biodegradable or biosoluble adhesive joins the distal tip portions together prior to insertion into the blood vessel and facilitates the separation of the distal tip portions from each other following insertion.

Another embodiment of the present invention provides a method for hemodialysis to include providing a multi-lumen catheter assembly with at least a blood extraction lumen and a blood return lumen extending longitudinally therethrough, each lumen having a proximal end adapted for coupling to a hemodialysis apparatus and a distal end terminating in separable distal tip portions for blood extraction and return where the tip portions are joined together by a biodegradable or biosoluble adhesive. The method further provides for inserting the distal end of the catheter assembly into a blood vessel and allowing the adhesive to degrade such that the distal tip portions separate from each other within the blood vessel.

Therefore, the present invention addresses current problems associated with conventional split-tip catheter insertion by joining the distal tips of a split-tip catheter with biodegradable or biosoluble adhesive. After insertion of the catheter into the patient, the biodegradable or biosoluble adhesive dissolves and the distal tips of the split-tip catheter are free to move and function like conventional split-tip, double lumen, triple lumen, or multi-lumen catheters.

BRIEF DESCRIPTION OF THE DRAWINGS

The invention will be more fully understood from the following detailed description taken in conjunction with the accompanying drawings, in which:

FIG. 5C is a schematic, perspective view of an embodiment of the present invention showing one lumen wound about another lumen;

FIG. 6A is a schematic, perspective view of an embodiment of the present invention showing fluid openings in the distal tip portions;

DETAILED DESCRIPTION OF THE INVENTION

As used herein, the term "bioresorbable" refers to materials that are biodegradable or biosoluble such that they degrade or break down by mechanical degradation upon interaction with a physiological environment into components that are metabolizable or excretable over a period of time.

Figure 1A:
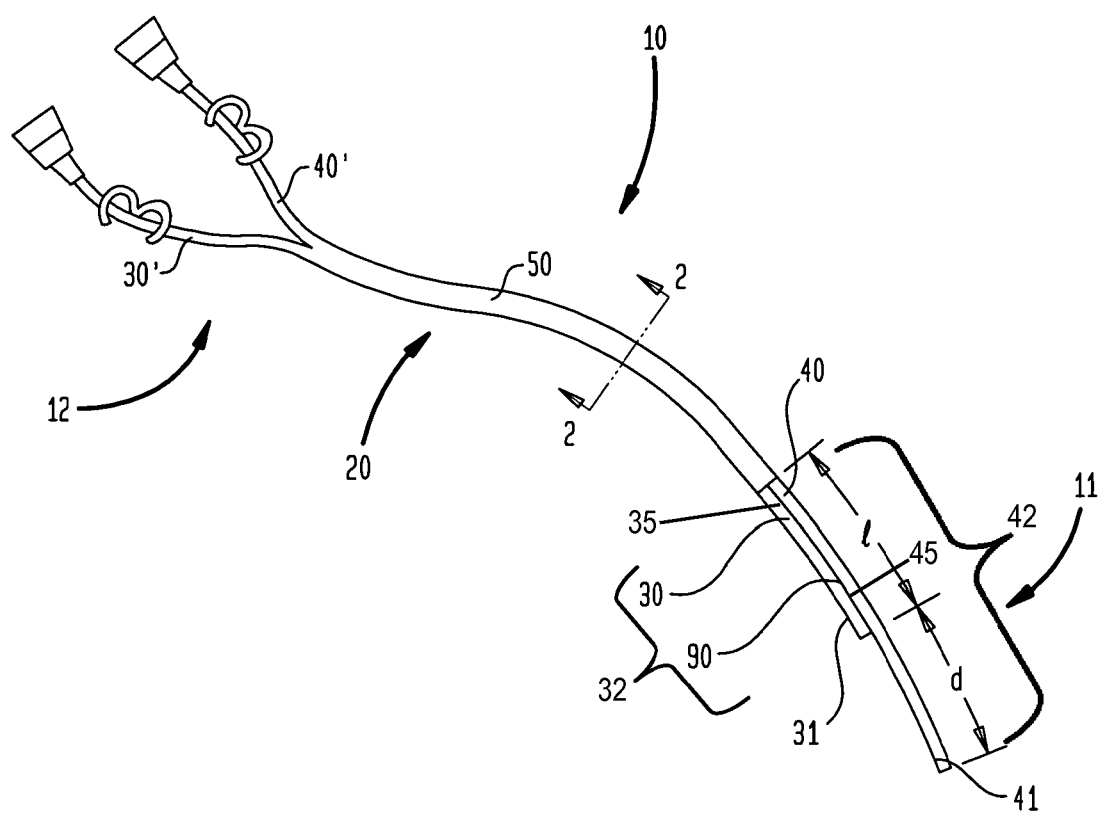
FIG. 1A is a schematic, perspective view of an embodiment of the present invention showing distal tip portions joined together.
Figure 1B:
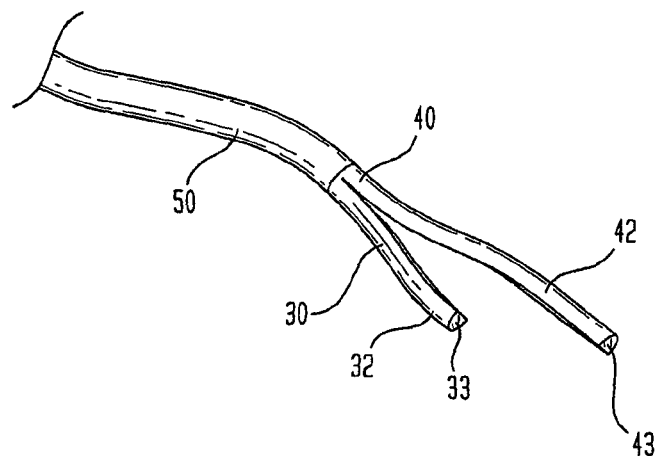
FIG. 1B is a schematic, perspective view of an embodiment of the present invention showing distal tip portions separated from one another.
Figure 1C:
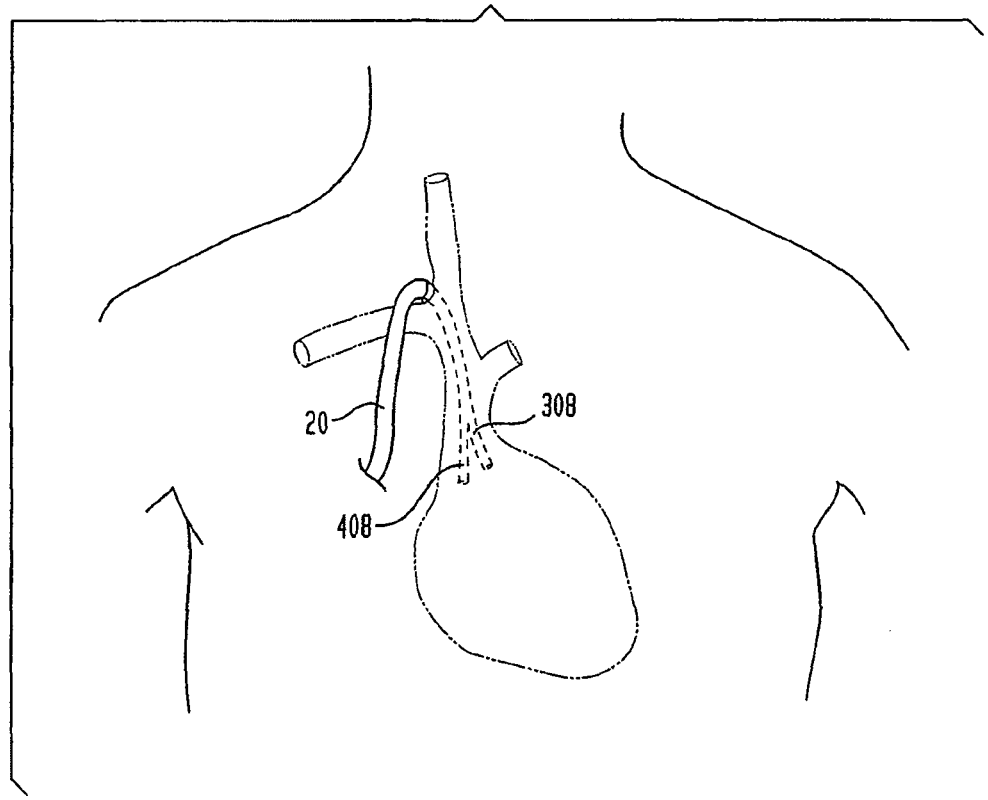
FIG. 1C is a schematic view of an embodiment of the present invention in use in the body of a patient.

The present invention includes various embodiments of a multi-lumen catheter for hemodialysis and methods of use. As shown in FIGS. 1A and 1B, one embodiment of catheter 10 includes an elongate body 20 having proximal and distal end 11 and 12, and at least one blood extraction lumen 30 and at least one blood return lumen 40 extending longitudinally therethrough. Each lumen 30, 40 has a proximal end 30', 40' adapted to direct fluid to, or couple directly with, a hemodialysis apparatus (not shown), and a distal end 31, 41 for insertion into a blood vessel. Distal extraction and return tip portions 32, 42 of each lumen 30, 40 include a distal end opening 33, 43 formed therein to provide for simultaneous flow of blood in opposite directions during hemodialysis. The distal extraction and return tip portions 32, 42 are joined by bioresorbable adhesive 90 prior to being inserted into a blood vessel such that after insertion, the bioresorbable adhesive degrades sufficiently to allow the distal extraction and return tip portions of each lumen 30, 40 to separate from one another.

Figure 2A:
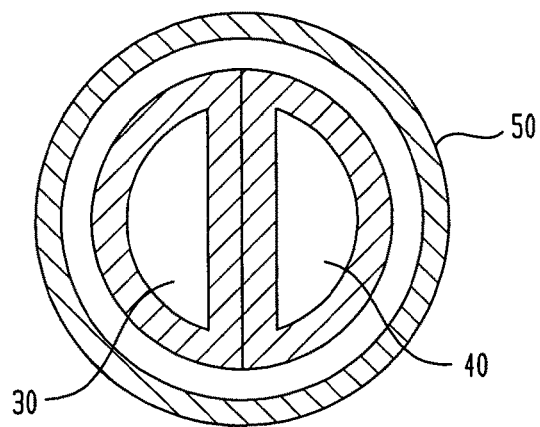
FIG. 2A is a cross-section view of an embodiment of the present invention showing opposed "D" shaped lumens inside an outer sheath.

FIGS. 1A and 1B illustrate an outer sheath 50 which covers and encloses the lumens 30, 40. The outer sheath 50 can be any shape and size and can be made of the same material as the lumens 30, 40 or other material compatible with insertion into a blood vessel. As illustrated in the embodiment shown in FIGS. 1A and 1B, the outer sheath 50 terminates proximal to the distal ends 31, 41 of the lumens 30, 40 such that the distal extraction and return tip portions 32, 42 of each lumen can separate from one another after being inserted into a blood vessel. FIG. 2A shows a cross-section 2-2 of one embodiment of an outer sheath 50. The outer sheath 50 can be any thickness and can have varying inner and outer shapes as well as varying inner and outer dimensions.

Figure 2B:
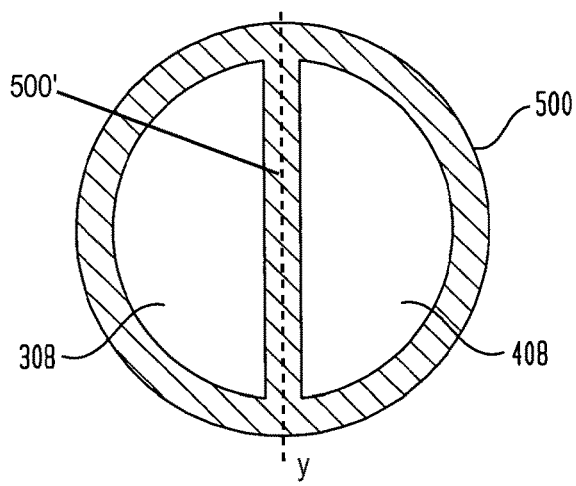
FIG. 2B is a cross-section view of an embodiment of the present invention showing unibody construction utilizing opposed "D" shaped lumens.

FIG. 2B illustrates another embodiment showing a cross-section of an elongate body 20 having unibody construction 500 which incorporates the blood extraction and blood return lumens 308, 408 in a single elongate body 20. The unibody catheter can be constructed such that sheath material 500' separates the lumens 308, 408. The amount of sheath material around each lumen 308, 408 and in-between each lumen can vary but preferably allows for blood extraction and blood return in accordance with hemodialysis. Separating the sheath material in-between both lumens 308, 408 along a vertical axis y at one end of the unibody construction can separate the lumens from one another into distinct distal portions. A variety of methods known to one skilled in the art can be used to separate the material such as for example cutting or scoring.

Figure 3A:
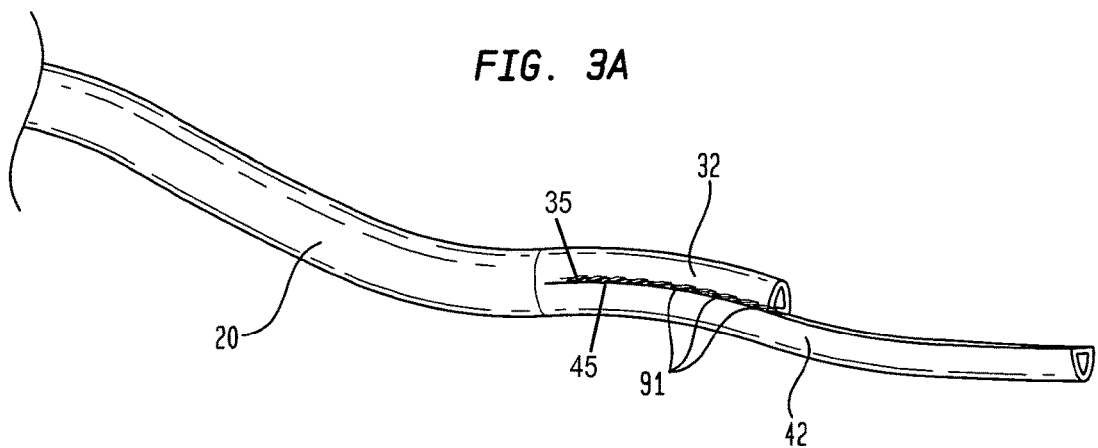
FIG. 3A is a schematic, perspective view of an embodiment of the present invention showing an adhesive application using spots of adhesive.
Figure 3B:
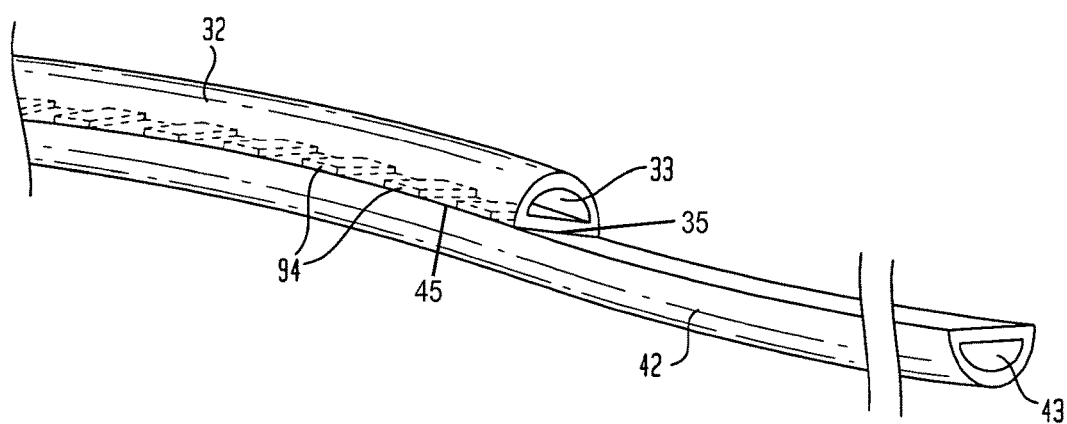
FIG. 3B is a schematic, perspective view of an embodiment of the present invention showing an adhesive application using regions of adhesive.
Figure 4A:
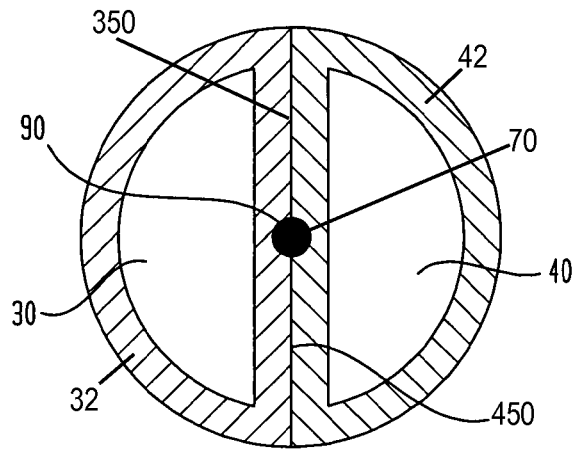
FIG. 4A is a cross-section view near the distal end of a catheter according to the present invention showing distal tip portions adhered to one another.
Figure 6B:
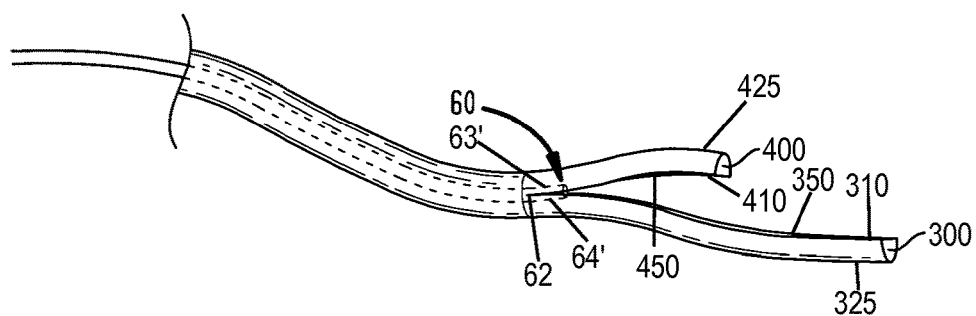
FIG. 6B is a schematic, perspective view of an embodiment of the present invention showing a design having an additional center lumen.
Figure 6C:
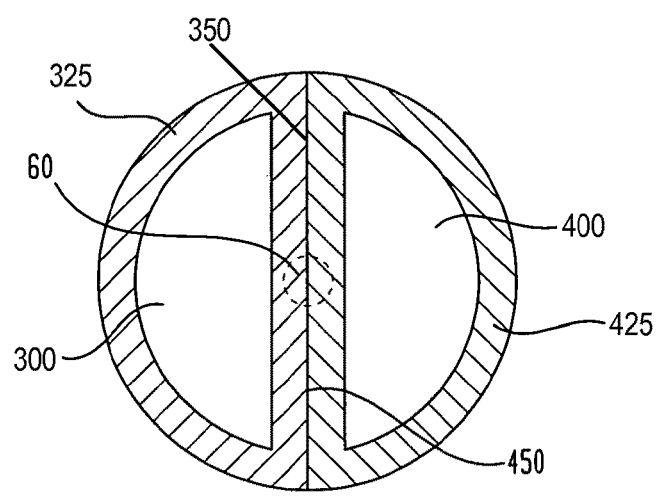
FIG. 6C is a cross-sectional view of an embodiment of the present invention showing a design having an additional center lumen.

In another embodiment of the present invention the elongate body 20 can be formed such that the blood extraction and blood return lumens 30 and 40 (or 300 and 400) are non-circular to increase the areas of their outer surfaces 350, 450 that are in contact as shown, for example, in cross-section in FIGS 4A and 6C. Here, the distal extraction and return tip portions 320, 420 of each lumen can have bioresorbable adhesive on all or any part of their facing surfaces 350, 450. As shown in FIG. 3A and 3B, the facing surfaces can be joined by spots 91 as well as regions 94 of adhesive (further described below). The configuration of the lumens in this embodiment allows the lumens, as joined, to resemble a single, circular lumen prior to insertion. After insertion of the distal extraction and return tip portions (e.g., tip portions 32 and 42 or tip portions 325 and 425), into a blood vessel, the bioresorbable adhesive 90 can dissolve allowing the tip portions to separate and facilitate hemodialysis.

Figure 2C:
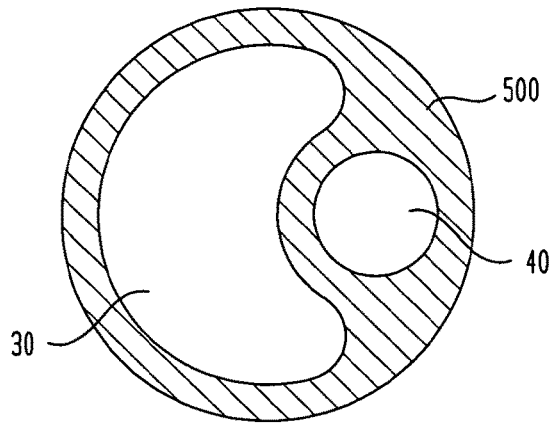
FIG. 2C is a cross-section view of an embodiment of the present invention showing yet another unibody construction.
Figure 2D:
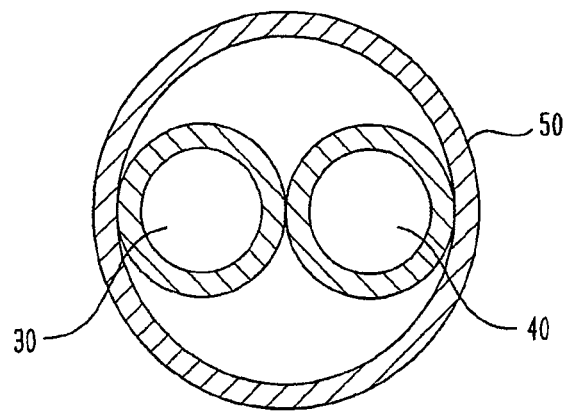
FIG. 2D is a cross-section view of an embodiment of the present invention showing individual lumens inside an outer sheath.
Figure 2E:
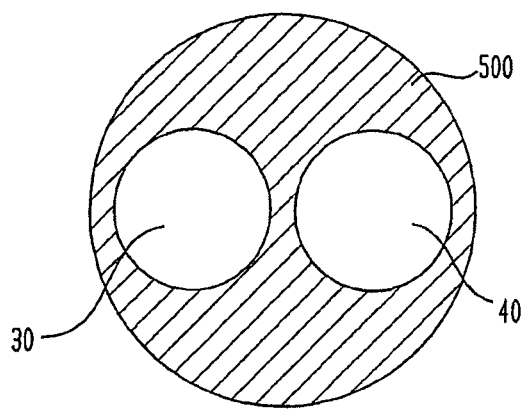
FIG. 2E is a cross-section view of an embodiment of the present invention showing a unibody construction utilizing individual lumens.
Figure 2F:
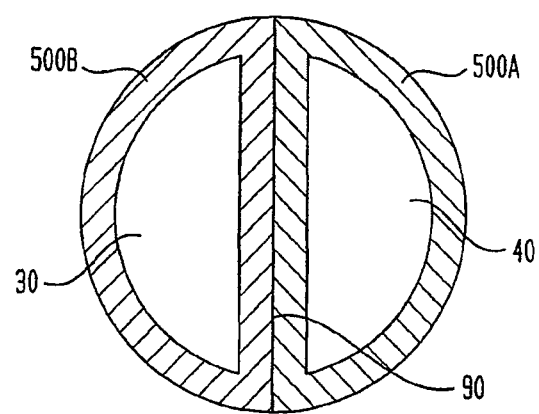
FIG. 2F is a cross-section view of a variation of an embodiment of the present invention showing opposed "D" shaped lumens.
Figure 2G:
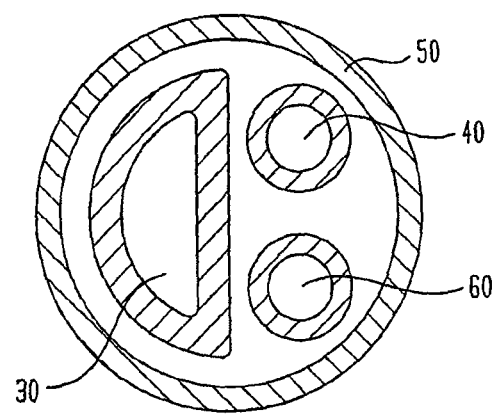
FIG. 2G is a cross-section view of an embodiment of the present invention showing three lumens.
Figure 2H:
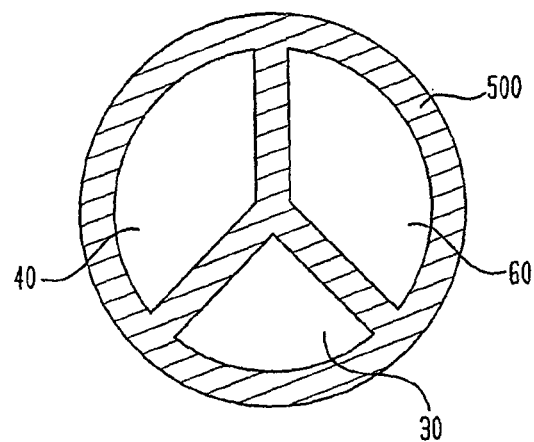
FIG. 2H is a cross-section view of a variation of an embodiment of the present invention showing three lumens.
Figure 2I:
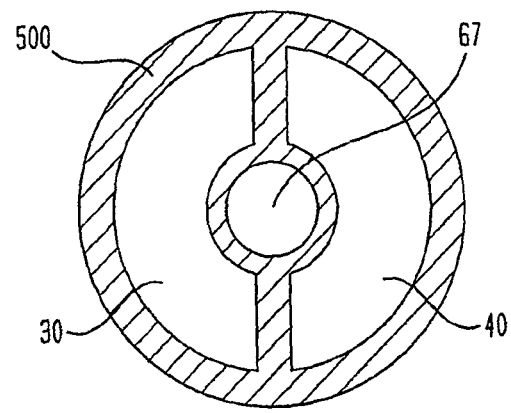
FIG. 2I is a cross-section view of a yet another variation of an embodiment of the present invention showing three lumens.

The lumens 30, 40 can have a variety of cross-sectional shapes and sizes but preferably, as shown in the embodiments in FIGS. 1B, 2A, 2B, 2F, 3A, 3B, 4A, 4C, 6B, 6C, 7A, and 7B, the lumens are "D" shaped. Alternately, each of the lumens 30, 40 can have a cross-sectional shape, size, or area that can be distinct from the other, as shown, for example, in FIGS. 2C, 2G, and 2H. FIG. 2A is a cross-section view of an embodiment of the present invention showing opposed "D" shaped lumens inside an outer sheath. FIG. 2B is a cross-section view of an embodiment of the present invention showing unibody construction utilizing opposed "D" shaped lumens. FIG. 2C is a cross-section view of an embodiment of the present invention showing yet another unibody construction. FIG. 2D is a cross-section view of an embodiment of the present invention showing individual lumens inside an outer sheath. FIG. 2E is a cross-section view of an embodiment of the present invention showing a unibody construction utilizing individual lumens. FIG. 2F is a cross-section view of a variation of an embodiment of the present invention showing opposed "D" shaped lumens. FIG. 2G is a cross-section view of an embodiment of the present invention showing three lumens. FIG. 2H is a cross-section view of a variation of an embodiment of the present invention showing three lumens. FIG. 2I is a cross-section view of a yet another variation of an embodiment of the present invention showing three lumens. The lumens 30, 40 can be made of any material consistent with materials presently known for catheters including any material which allows the distal tip portions 32, 42 of the lumens to be flexible and facilitate hemodialysis.

The distal extraction and return tip portions 32, 42 of each lumen 30, 40 include distal end openings 33, 43 formed thereon for the extraction or return of blood or other bodily fluids. The openings are preferably sized to allow the carrying of blood to and from the hemodialysis unit. The distal extraction and return tip portions 32, 42 can be the same length or, as shown in FIGS. 1A and 1B, can be different lengths. As shown, the distal extraction tip portion 32 of the blood extraction lumen 30 terminates proximal to the distal return tip portion 42 of the blood return lumen 40. However, in another embodiment, the distal return tip portion 42 of the blood return lumen 40 can terminate proximal to the distal extraction tip portion 32 of the blood extraction lumen 30. The longitudinal distance d between the distal extraction and return tip portions 32, 42 of each lumen 30, 40 can vary but preferably allows for performing blood extraction and blood return in accordance with hemodialysis. Prior to the distal end 11 of the catheter being inserted into a blood vessel, the distal extraction and return tip portions 32, 42 of the lumens 30, 40 are joined to one another with bioresorbable adhesive 90. After insertion into the blood vessel, bioresorbable adhesive 90 facilitates the separation of the distal extraction and return tip portions 32, 42 of the lumens 30, 40.

The bioresorbable adhesive 90 used to join the distal extraction and return tip portions, 32, 42 of the lumens 30, 40 to one another can be a composition selected from the group of polymers consisting of polylactides, polyglycolides, polylactones, polyorthoesters, polyanhydrides, and copolymers and combinations thereof. In general, bioresorbable adhesives have bonding elements and degradable elements. The degradable elements can have the components of polylactide, polyglycolide and polylactones (polycaprolactone). The bonding elements can have hydrogen bonding strength (polyvinyl alcohol, polysaccharides) or can be able to polymerize as a single component (cyanoacrylates) or as two componets (epoxy compound plus amino compounds, or radical (light) initiators of acrylate compounds).

Proteins, sugars, and starch can also be used as an adhesive. By way of non-limiting example, antithrombotic agents such as heparin and hirudin, citrate, antithrombin-heparin complex, and albumin heparin complex as well as anti-infective agents such as chlorohexidine, silver, antibiotics, and antiseptic agents may be added to the adhesive.

In an embodiment of the present invention, polymers which can be useful include polyurethane, generally described as a copolymer of polyethylene glycol with polylactide or polyglycolide end capped with methacrylates. Another embodiment can include a two component composition, one component preferably including a low molecular weight polyurethane end capped with methacrylates, and the other component preferably including polylactide, polyglycolide, or polycaprolactone end capped with methacrylate.

In another embodiment of the present invention, one or more components can be used from styrene, methyl methacrylate, methyl acrylate, ethylene dimethacrylate, ethylene diacrylate, acrylamide, diurethane dimethacrylate, polyisoprenegraft-maleic acid monomethyl ester, azobis(cyanovaleric acid), azobiscyclohexanecarbonitrile, azobisisobutyronitrile, benzoyl peroxide, iron (II) sulfate, polyvinyl alcohol, dextran, polysaccharide, epichlorohydrin, ethylenediamine, diaminocyclohexane, diamino propane, copolymers with polylactide and polyethylene oxide as the blocks and acrylate, methacrylate as the end groups, cyanoacrylates, ethyl-2cyanoacrylate, propyl-2-cyanoacrylates, pentyl-2-cyanoacrylate, hexyl-2-cyanoacrylate, and octyl-2-cyanoacrylate, ammonium persulfate and/or polyethylene glycol methacrylate when water, organic solvent such as dichloromethane, chloroform, tetrahydrofuran, acetone, petroleum ether, acetyl acetate, dimethylformamide, or the mixture thereof, is combined with the aforementioned solvents.

As shown in FIGS. 1A, 3A, and 3B, bioresorbable adhesive can be applied along a facing surface 35, 45 of either, or both, distal extraction and return tip portions 32, 42 of the lumens 30, 40 to facilitate the joining of the lumens along their longitudinal length l prior to insertion of the distal end 11 of the catheter 10 into a blood vessel. (As used throughout, "catheter 10" refers to the various embodiments of the present invention.) FIG. 1A shows bioresorbable adhesive 90 applied along a longitudinal length l of the distal extraction and return tip portions 32, 42 of each lumen 30, 40. However, the bioresorbable adhesive 90 need not be applied along the entire length of the facing surfaces 35, 45 of each lumen 30, 40 but is preferably applied such that the adhesive facilitates the joining of the distal extraction and return tip portions 32, 42 of the lumens 30, 40 prior to insertion into a blood vessel and allows the distal extraction and return tip portions of the lumens to separate after insertion.

In the embodiments described herein, the bioresorbable adhesive 90 preferably dissolves after insertion into a blood vessel to provide separation of the distal extraction and return tip portions 32, 42 of the lumens 30, 40 in a time period ranging from 1 minute to 1 hour. This range can be controlled by using different compositions of the bioresorbable adhesive 90 as well as by the amount of adhesive applied to join the distal extraction and return tip portions 32, 42 of the lumens 30, 40 together. In another embodiment with opposed distal fluid openings 80 (further described below), the bioresorbable adhesive 90 can be water soluble such that the introduction of saline or similar type fluid will effectuate the separation of the distal extraction and return tip portions 32, 42 of the lumens 30, 40. In this instance, the adhesive will not dissolve until a time after the introduction of the soluble solution into the lumens 30, 40.

As shown in another embodiment in FIG. 3A, the bioresorbable adhesive can also be applied to the facing surfaces of the distal extraction and return tip portions 32, 42 of the lumens 30, 40 in form as discrete spots 91. The spots 91 of bioresorbable adhesive 90 can be applied continuously along the entire longitudinal length l of the distal extraction and return tip portions 32, 42 of the lumens 30, 40 or selectively in an assortment of areas thereof. Preferably, the bioresorbable adhesive 90 is applied such that the spots 91 of adhesive facilitate the joining of the distal extraction and return tip portions 32, 42 of the lumens 30, 40 prior to insertion into a blood vessel and allow the distal extraction and return tip portions of the lumens to separate after insertion. The spots 91 of bioresorbable adhesive 90 can vary in number and size in order to facilitate the joining of the tip portions of the lumens.

FIG. 3B shows yet another embodiment of the application of the bioresorbable adhesive 90 in the form of discrete regions 94. Discrete regions 94, like the spots 91 stated above, of bioresorbable adhesive 90 can be applied to the facing surfaces of the distal extraction and return tip portions 32, 42 of the lumens 30, 40. The discrete regions 94 of bioresorbable adhesive 90 can also be different lengths and can be applied in addition to discrete spots 91 of adhesive such that the adhesive facilitates the joining of the distal extraction and return tip portions 32, 42 of the lumens 30, 40 prior to insertion into a blood vessel and allows the distal extraction and return tip portions of the lumens to separate after insertion.

Figure 4B:
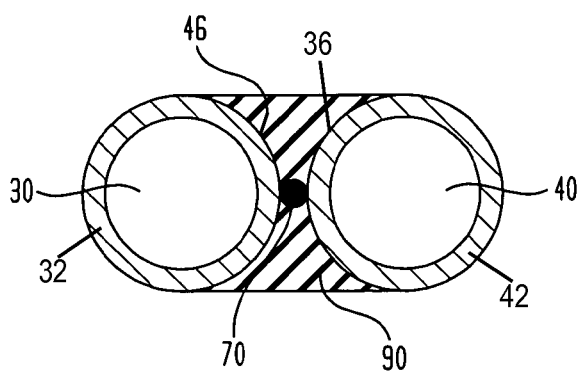
FIG. 4B is an distal cross-sectional view of another embodiment of the present invention showing alternative adhesive disposition.
Figure 4C:
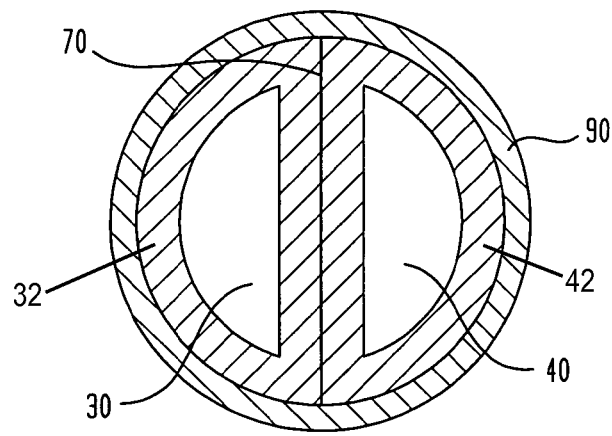
FIG. 4C is a distal cross-sectional view of yet another adhesive design.

FIGS. 4A-4C show cross-sections of the distal extraction and return tip portions 32, 42 of the lumens 30, 40 detailing alternate embodiments of the bioresorbable adhesive 90 application. FIG. 4A shows bioresorbable adhesive 90 applied at the contact point 70 of the facing surfaces 350, 450 of the lumens 30, 40. FIG. 4B shows another embodiment of an application of the bioresorbable adhesive 90 such that the adhesive, as applied, joins non-contacting surfaces 36, 46 of the distal extraction and return tip portions 32, 42 of the lumens 30, 40. FIG. 4C shows a variation on the embodiment shown in FIG. 4A where the bioresorbable adhesive 90 surrounds the distal extraction and return tip portions 32, 42 of the lumens 30, 40 forming a continuous cross-section of adhesive coating notwithstanding the distal extraction and return tip portions of the lumens extending therethrough. As stated above, the bioresorbable adhesive 90 need not be applied along the entire length of the distal extraction and return tip portions 32, 42 of each lumen 30, 40 but is preferably applied such that the adhesive facilitates the joining of the distal extraction and return tip portions of the blood extraction and blood return lumens prior to insertion into a blood vessel and allows the distal extraction and return tip portions of the lumens to separate after insertion. It should be noted that because the lumens 30, 40 can be various shapes, as stated above, the bioresorbable adhesive 90 need not be applied to all of the contact area along length l of the facing surfaces 35, 45 of each lumen 30, 40, as shown in FIG. 1A. As shown in FIGS. 3A and 3B, the bioresorbable adhesive 90 can be applied as a region 94, spot 91, or other shape, to a section of the contact area and need only be applied to facilitate the joining function.

Figure 5A:
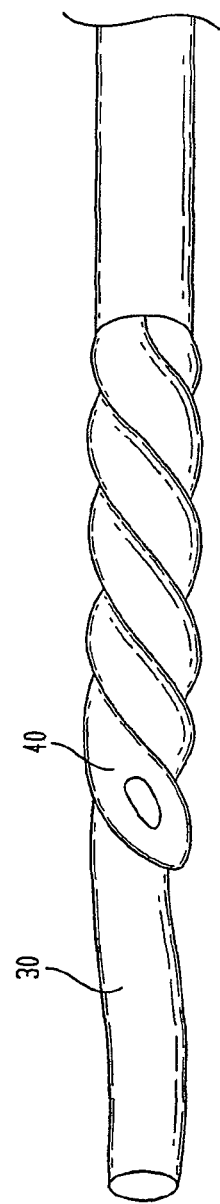
FIG. 5A is a schematic, perspective view of another embodiment of the present invention showing distal tip portions joined and wound about one another.
Figure 5B:
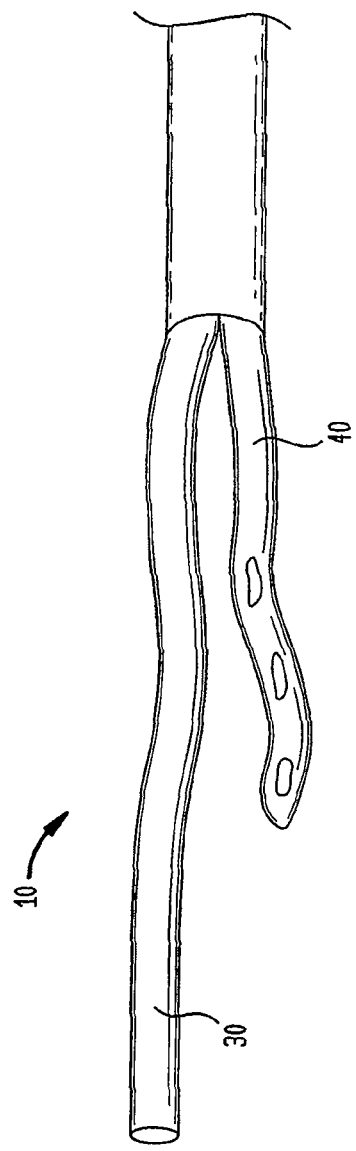
FIG. 5B is a schematic, perspective view of the embodiment of FIG. 5A with the distal tip portions shown in a separated state.

FIG. 5A illustrates another embodiment of the present invention. As shown, the lumens 30, 40 are twisted about, or otherwise wrapped, around one another. The wrapped lumens can be twisted about one another such that there are non-contact areas, along the longitudinal length l of the distal extraction and return tip portions of each lumen 30, 40 as shown in FIG. 5A. In FIG. 5B, the distal tip elements are shown in a separated state. The distal extraction and return tip portions of each lumen 30, 40 can wrap around one another any number of times, as well as wrap such that one lumen 30 is wound around the other lumen 40 as shown in FIG. 5C, or vice versa. In FIG. 5A, bioresorbable adhesive 90 can be applied where the distal extraction and return tip portions of the lumens 30, 40 contact one another. As stated above, the bioresorbable adhesive 90 can be applied in discrete spots or regions where the distal extraction and return tip portion surfaces contact one another. However, the bioresorbable adhesive need not be applied to all contact points of the twisted lumens 30, 40 so long as the joining of the distal extraction and return tip portions of the lumens 30, 40 can be facilitated. The various compositions and methods of application of the bioresorbable adhesive 90 application previously described above can also be used with the twisted embodiment catheter design as well.

In another embodiment of the present invention, FIG. 6A shows distal fluid openings 80, in formed in the distal extraction tip portion 32 of lumen 30. It should be understood from the drawings that in the embodiment shown, the distal fluid openings 80 can either be in addition to, or in place of, the distal end opening 33 located on the distal extraction tip portion 32 of lumen 30. The distal fluid openings 80 can be any shape and size and can be located in a variety of places on lumen 30 as illustrated. However, FIG. 6A shows the distal fluid openings 80 located on facing (contacting) surface 35 of the distal extraction tip portion 32 of lumen 30. In this embodiment, the distal fluid openings 80 can be filled or covered with fluid activated bioresorbable adhesive 900 and joined to lumen 40 along its facing surface 45. After insertion of the catheter into a blood vessel, saline or similar type fluid can be introduced into lumen 30 at its proximal end 30' such that the fluid travels through the lumen to the distal fluid openings 80 and dissolves the fluid activated bioresorbable adhesive 900 thereby separating the distal extraction and return tip portions 32, 42 along their longitudinal length l to facilitate hemodialysis. Bioresorbable adhesive 90 can also be applied to the contact surfaces 35, 45 of each lumen as previously described above in addition to the distal fluid openings 80 being filled or covered with fluid activated bioresorbable adhesive 900.

FIG. 6B shows yet another embodiment in which the catheter 10 can be designed to facilitate separation of its distal tips 325, 425 after insertion into a blood vessel. Catheter 10 can include a center lumen 60 extending in-between lumens 300, 400 from a proximal end 120 to a separation point 62 and can be used to carry saline or a similar type fluid. At the separation point 62, the center lumen splits into two center lumen halves 63', 64' each half located in a facing surface 350, 450 of each lumen 300, 400. The center lumen 60 can be made of a variety of cross-sectional shapes but is preferably circular. As shown, the center lumen halves 63', 64' terminate proximal to the distal ends 310, 410 of lumens 300, 400. It should be noted that a mirrored portion of center lumen half 64' is located in the facing surface 450 of distal return tip 425. The proximal end of center lumen 60, which is out of view in FIG. 6B, can extend at the proximal end 120 of catheter 10 anywhere outside the patient so long as the center lumen 60 can be accessible for saline fluid introduction. As shown in FIG. 6C, the center lumen 60 and the center lumen halves 63', 64' are not in fluid communication with either of the lumens 300, 400. Distal extraction and return tip portions 325, 425 can have fluid activated bioresorbable adhesive 900 applied anywhere within center lumen halves 63', 64' distal of a center lumen gap. The adhesive 900 can also be applied at or beyond a center lumen half end, to facilitate separation of the distal tip portions 325, 425. The center lumen gap, of any desirable length, should remain free of fluid activated bioresorbable adhesive 900 and in fluid communication with a blood vessel in order to allow any extraneous saline or similar type fluid to be displaced between the facing surfaces 350, 450 and into the bloodstream during the dissolving process.

In this embodiment, the catheter 10 is inserted into a patient and saline or other type fluid can be introduced into the center lumen 60 at its proximal end which dissolves the fluid activated bioresorbable adhesive 900 applied at or beyond center lumen gap. Once separated, the distal tip portions 325, 425 can facilitate blood extraction and blood return in accordance with hemodialysis through distal end openings of lumens 300, 400.

Figure 7A:
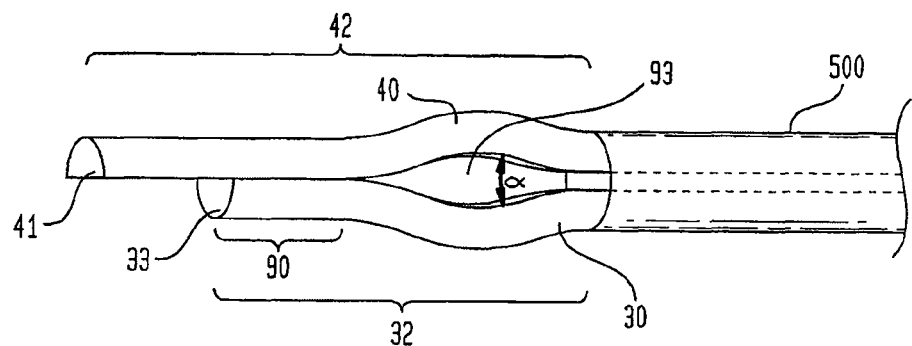
FIG. 7A is a schematic, perspective view of an embodiment of the present invention showing distal tip portions adhered to one another in a shape memory configuration.
Figure 7B:
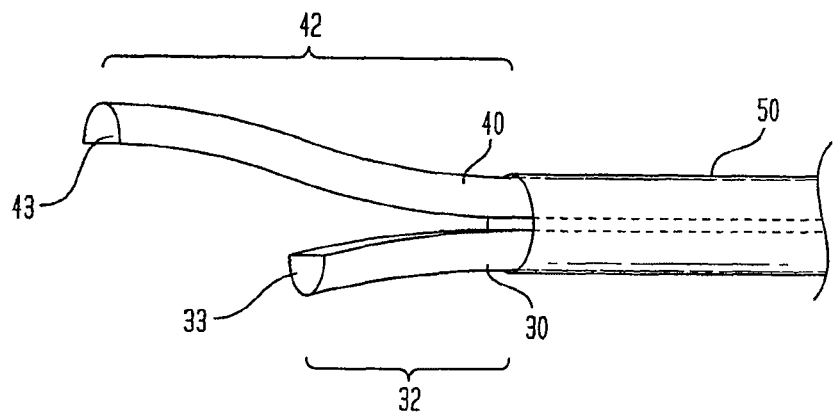
FIG. 7B is a schematic, perspective view of the embodiment in FIG. 7A showing distal tip portions that are separated.

In FIGS. 7A and 7B, another embodiment of the present invention is shown in which one or both of the lumens 30, 40 can be made of a shape memory material such that after insertion of the distal end 11 of the device into a blood vessel, and upon the bioresorbable adhesive 90 dissolving, the lumens, and more preferably the distal extraction and return tip portions 32, 42 thereof, can separate to a pre-adhesive position. The distal extraction and return tip portions 32, 42 of the lumens 30, 40 can be made of polymer material or other material as needed or combined to facilitate the shape memory in the described embodiment. FIGS. 7A and 7B illustrate the lumens 30, 40 in this configuration. The distal extraction and return tip portions 32, 42 of each lumen 30, 40 are joined with bioresorbable adhesive 90 prior to insertion into a blood vessel. A memory gap 93 can be located between the lumens and distal of the outer sheath 50. The memory gap can be any length and width but preferably allows for a configuration such that the lumens 30, 40 are not pinched after joining. As shown, each lumen 30, 40 exits the outer sheath 50 in a non-parallel, diverging direction. The relative angle α at which the lumens 30, 40 exit the outer sheath 50 can vary. Bioresorbable adhesive 90 can be applied, in any manner described herein, to join the lumens 30, 40 distal of the memory gap 93. FIG. 7B shows the lumens 30, 40 in roughly a "pre-adhesive" configuration as well as in an "after insertion into a blood vessel" configuration. It should be noted that the lumens 30, 40 illustrated in FIG. 7B, can separate more or less, after being inserted into a blood vessel, as compared to their pre-adhesive state.

Figure 8:
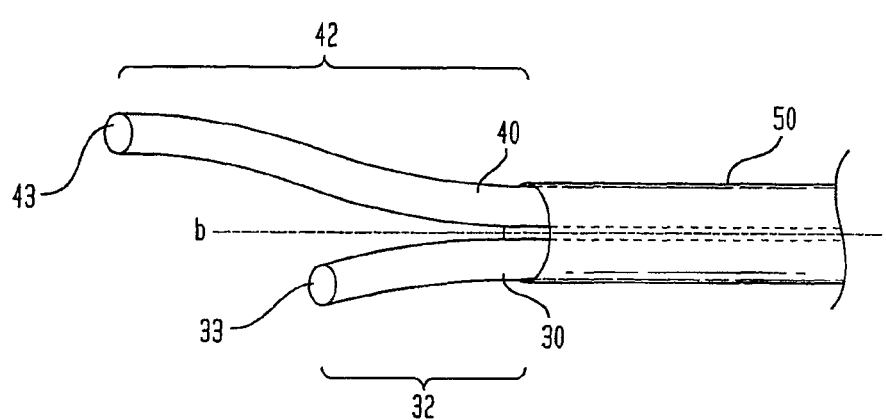
FIG. 8 is schematic, perspective view of an embodiment of the present invention showing distal tip portions in an alternate shape memory configuration.

In another embodiment, the distal extraction and return tip portions 32, 42 of each of the lumens 30, 40 can be pre-formed to exit the outer sheath 50 in a substantially parallel direction and then angularly diverge from one another, at a location distal from the outer sheath, upon the degradation of the bioresorbable adhesive 90, as shown in FIG. 8. The distal extraction and return tip portions 32, 42 of each lumen 30, 40 shown in FIG. 8, exit the outer sheath 50 in a distal direction and are substantially parallel relative to one another. As the bioresorbable adhesive 90, applied in any manner described herein, dissolves, the distal extraction and return tip portions 32, 42 of the lumens 30, 40 substantially separate and angularly diverge from one another along a longitudinal axis b. Distal extraction and return tip portions 32, 42 of each lumen 30, 40 can be pre-formed from polymer or similar type polymer materials to effectuate this divergence. As further shown in FIG. 7, the distal extraction and return tip portions 32, 42 can re-converge toward each other if desired or can continue diverging as shown in FIG. 6B.

In use, a catheter 10 is provided having distal extraction and return tip portions 32, 42 which are joined to one another using any of the bioresorbable adhesive applications described throughout this specification. The proximal end 12 of the catheter 10 can be attached to a hemodialysis apparatus using various attachment means known to one skilled in the art. The distal end 11 of the catheter 10 can be inserted into a blood vessel wherein the bioresorbable adhesive 90 is allowed to dissolve in a time in the range of 1 minute to 1 hour, such that the distal extraction and return tip portions 32, 42 of the blood extraction lumen 30 and the blood return lumen 40 separate from each other within the blood vessel. Blood extraction and blood return can be subsequently commenced through each lumen 30, 40 according to hemodialysis methods and practices.

Accordingly, the embodiments of the present invention are not limited by what has been particularly shown and described, except as indicated by the appended claims. All publications and references cited herein are expressly incorporated herein by reference in their entirety.

What is claimed is:

1. A multi-lumen catheter device for hemodialysis, comprising:
   an elongate catheter body with at least a blood extraction lumen and a blood return lumen extending longitudinally therethrough, having a proximal end adapted for coupling to a hemodialysis apparatus, and having a distal end terminating in separable distal tip portions adapted for insertion in a blood vessel, the distal end further comprising:
   a distal extraction tip portion for fluidic coupling of the blood extraction lumen with the blood vessel;
   a distal return tip portion for fluidic coupling of the blood return lumen with the blood vessel;
   at least one gap between the distal extraction tip portion and the distal return tip portion that facilitates the entry of fluid between the distal tip portions; and
   a bioresorbable adhesive located between the separable distal tip portions distal to the at least one gap, the adhesive configured to join the distal tip portions together for insertion into the blood vessel while maintaining the at least one gap between the distal tip portions, the bioresorbable adhesive dissolvable in blood of the blood vessel, thereby facilitating separation of the distal tip portions from each other following insertion.

2. The device of claim 1, wherein the blood extraction and blood return lumens are independent of each other to provide simultaneous flow of blood in opposite directions during hemodialysis.

3. The device of claim 1, wherein the bioresorbable adhesive comprises a hydrophilic polymer.

4. The device of claim 1, wherein the bioresorbable adhesive comprises a water-soluble composition.

5. The device of claim 1, wherein the bioresorbable adhesive degrades in blood to provide separation of the distal tip portions from each other in less than an hour.

6. The device of claim 1, wherein the bioresorbable adhesive degrades in blood in a time period ranging from about 1 second to about 7 days.

7. The device of claim 1, wherein the bioresorbable adhesive degrades in blood in a time period ranging from about 1 second to about 1 day.

8. The device of claim 1, wherein the bioresorbable adhesive degrades in blood in a time period ranging from about 1 second to about 1 hour.

9. The device of claim 1, wherein the bioresorbable adhesive comprises a composition selected from a group consisting of polylactides, polyglycolides, polylactones, polyorthoesters, polyanhydrides, and copolymers thereof.

10. The device of claim 1, wherein the bioresorbable adhesive comprises a protein, a sugar, and a starch.

11. The device of claim 1, wherein the bioresorbable adhesive comprises an antithrombotic, an anti-septic, or an anti-stenotic agent.

12. The device of claim 1, wherein the distal tip portions are of different lengths.

13. The device of claim 1, wherein the blood extraction and blood return lumens have different cross-sectional areas.

14. The device of claim 1, wherein at least one of the distal tip portions has a plurality of openings for fluid flow.

15. The device of claim 1, wherein the elongate catheter body has an unibody construction with the blood extraction lumen and the blood return lumen incorporated therein.

16. The device of claim 1, wherein the blood extraction and the blood return lumens are separate tubular elements and partially joined by an outer sheath.

17. The device of claim 1, wherein the bioresorbable adhesive covers at least a portion of an outer surface of each distal tip portion.

18. The device of claim 1, wherein the bioresorbable adhesive applied to a surface of each distal tip portion forms a continuous linear bond.

19. The device of claim 1, wherein the bioresorbable adhesive applied to a surface of each distal tip portion forms discrete spots.

20. The device of claim 1, wherein at least one distal tip portion comprises a shape memory material.

21. The device of claim 20, wherein the shape memory material is configured to facilitate an angular separation of the distal tip portions from each other to a pre-adhesive position following dissolution of the bioresorbable adhesive.

22. The device of claim 1, wherein at least one of the distal tip portions is coiled about another of the distal tip portions.

23. The device of claim 1, wherein the elongate catheter body contains an additional lumen for fluid administration or sampling.

24. The device of claim 1, wherein the bioresorbable adhesive comprises a bonding element and a degradable element.

25. The device of claim 1, further comprising a third lumen extending longitudinally along a length of the device from the proximal end to a separation point between the distal tip portions, wherein the third lumen is designed such that fluid administered through the third lumen is directed from the third lumen at the bioresorbable adhesive located between the separable distal tip portions to facilitate the dissolution of the bioresorbable adhesive and separation of the distal tip portions.

* * * * *